(12) United States Patent
Weissman et al.

(10) Patent No.: US 11,718,670 B2
(45) Date of Patent: *Aug. 8, 2023

(54) METHODS FOR DETERMINING AND ACHIEVING THERAPEUTICALLY EFFECTIVE DOSES OF ANTI-CD47 AGENTS IN TREATMENT OF CANCER

(71) Applicant: The Board of Trustees of the Leland Stanford Junior University, Stanford, CA (US)

(72) Inventors: Irving L. Weissman, Stanford, CA (US); Mark P. Chao, Mountain View, CA (US); Ravindra Majeti, Palo Alto, CA (US); Jie Liu, Palo Alto, CA (US); Jens-Peter Volkmer, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/930,621

(22) Filed: Sep. 8, 2022

(65) Prior Publication Data

US 2023/0068235 A1 Mar. 2, 2023

Related U.S. Application Data

(63) Continuation of application No. 16/089,115, filed as application No. PCT/US2017/027662 on Apr. 14, 2017, now Pat. No. 11,472,878.

(60) Provisional application No. 62/427,679, filed on Nov. 29, 2016, provisional application No. 62/323,330, filed on Apr. 15, 2016.

(51) Int. Cl.
| | | |
|---|---|---|
| *A61K 35/00* | (2006.01) | |
| *C07K 16/28* | (2006.01) | |
| *A61P 35/00* | (2006.01) | |
| *A61K 9/00* | (2006.01) | |
| *G01N 33/68* | (2006.01) | |
| *A61K 39/00* | (2006.01) | |

(52) U.S. Cl.
CPC ........ *C07K 16/2803* (2013.01); *A61K 9/0019* (2013.01); *A61P 35/00* (2018.01); *G01N 33/6854* (2013.01); *A61K 2039/505* (2013.01);

*A61K 2039/545* (2013.01); *C07K 2317/24* (2013.01); *G01N 2333/70503* (2013.01)

(58) Field of Classification Search
None
See application file for complete search history.

(56) References Cited

U.S. PATENT DOCUMENTS 9,623,079 B2 4/2017 Willingham et al.

FOREIGN PATENT DOCUMENTS

| WO | WO2014/149477 | 9/2014 |
|---|---|---|
| WO | WO2014149477 | * 9/2014 |
| WO | WO2014/160753 | 10/2014 |
| WO | WO2014/179132 | 11/2014 |
| WO | WO2015/050983 | 4/2015 |
| WO | WO 2015/105995 | 7/2015 |
| WO | WO2016/028810 | 2/2016 |

OTHER PUBLICATIONS

Liu et al (2015) "Pre-Clinical Development of a Humanized Anti-CD47 Antibody with Anti-Cancer Therapeutic Potential", Plos One, vol. 10, No. 9, pp. 1-23.
Morrison et al. (2020) "Industry shows increased appetite for macrophage biology",Nature Reviews Drug Discovery, Nature Publishing Group, GB, vol. 19, No. 5, pp. 295-297.
Siegel et al., (2016) "Cancer Statistics", CA: A Cancer Journal for Clinicians, 66(1), American Cancer Society, Atlanta, GA, pp. 7-30.
Sternebring et al. (2016) "A Weighted Method for Estimation of Receptor Occupancy for Pharmacodynamic Measurements in Drug Development", Clinical Cytometry, pp. 220-229, vol. 90, Issue 2, Wilely, Hoboken NJ.
Urger et al. (2019) "Blockade of the CD47-SIRP[alpha] axis: a promising approach for cancer immunotherapy", Expert Opinion on Biological Therapy, vol. 20, No. 1, pp. 5-8, XP055731509.
Kaur et al. (2020) "Preclinical and clinical development of therapeutic antibodies targeting functions of CD47 in the tumor microenvironment", Antibody Therapeutics, vol. 3, No. 3, pp. 179-192.

* cited by examiner

*Primary Examiner* — Meera Natarajan
(74) *Attorney, Agent, or Firm* — Pamela J. Sherwood; Bozicevic, Field & Francis LLP

(57) ABSTRACT

Methods are provided for treating a subject with an anti-CD47 agent.

14 Claims, 11 Drawing Sheets

FIG. 3B
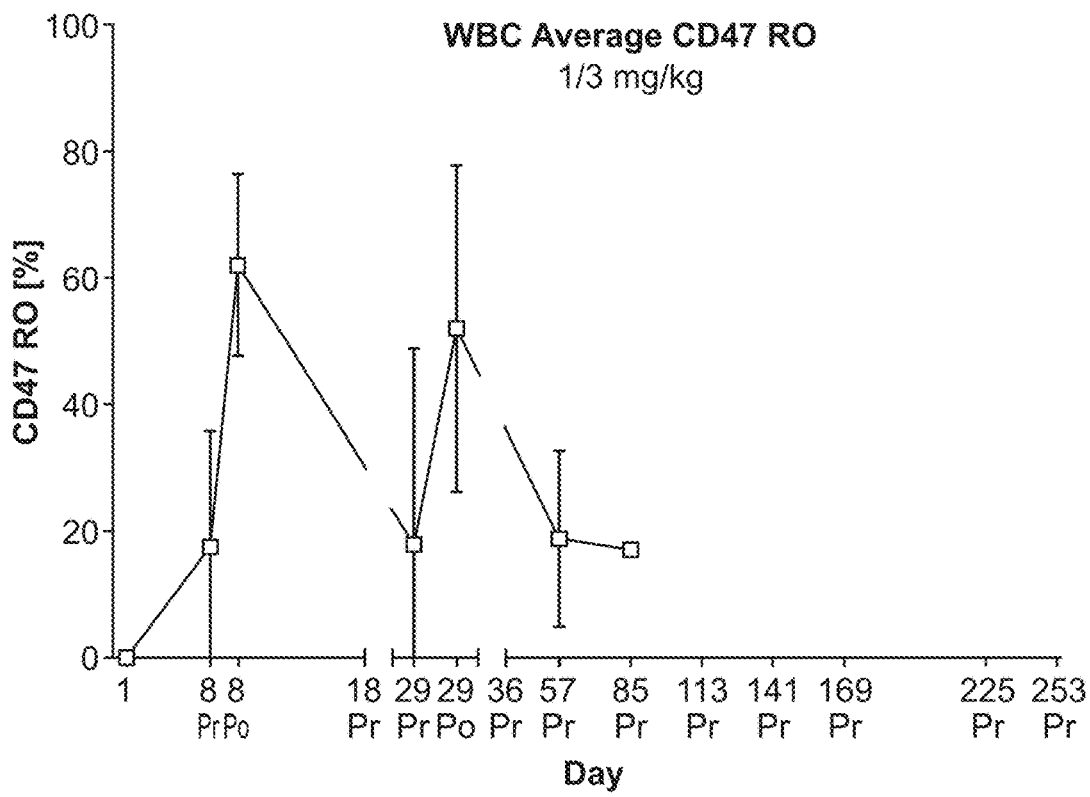
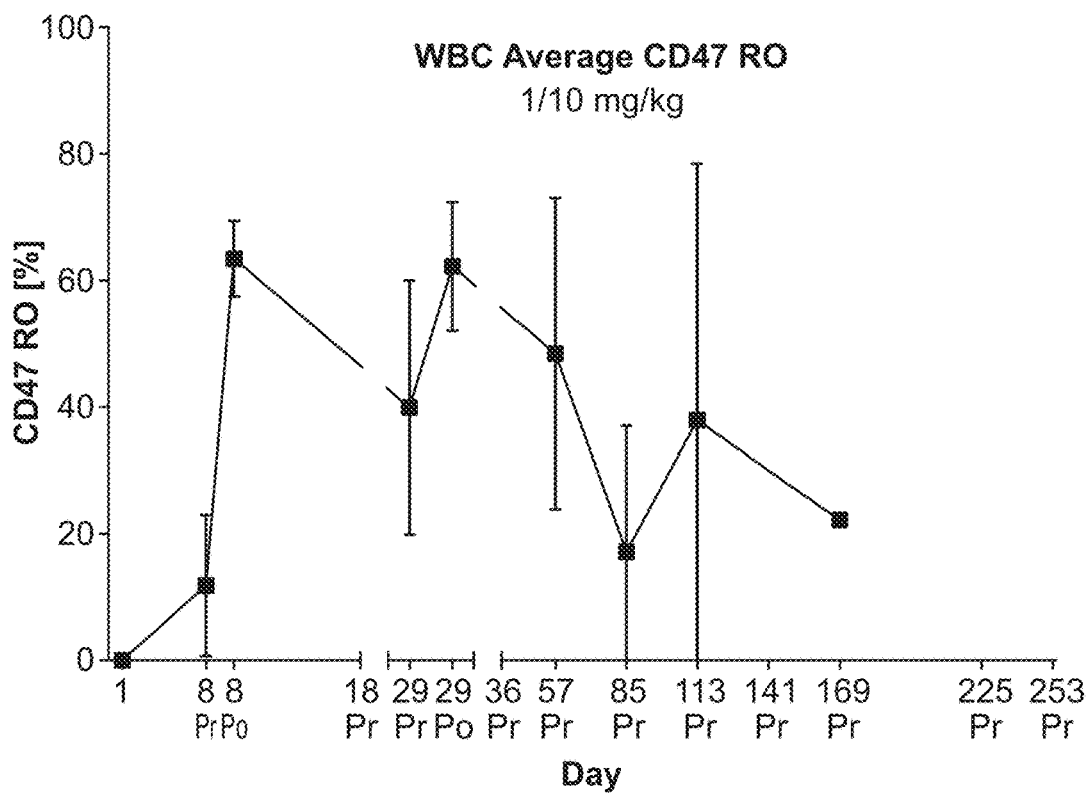

FIG. 3C
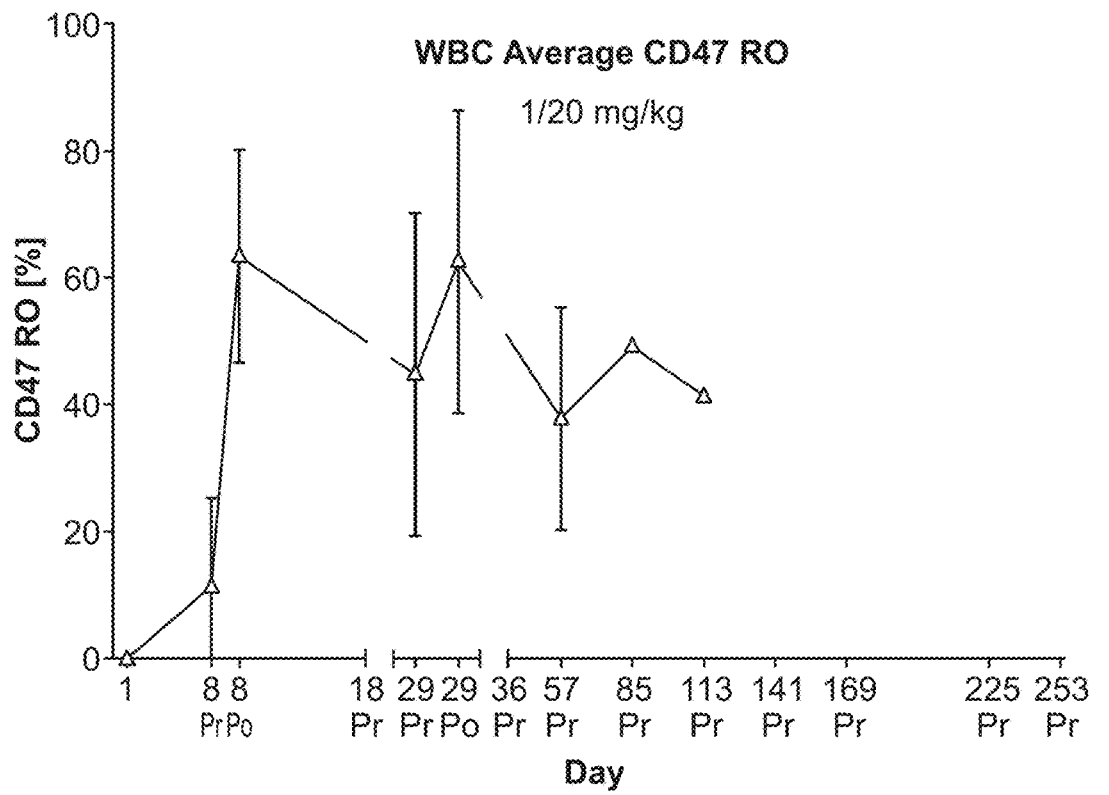
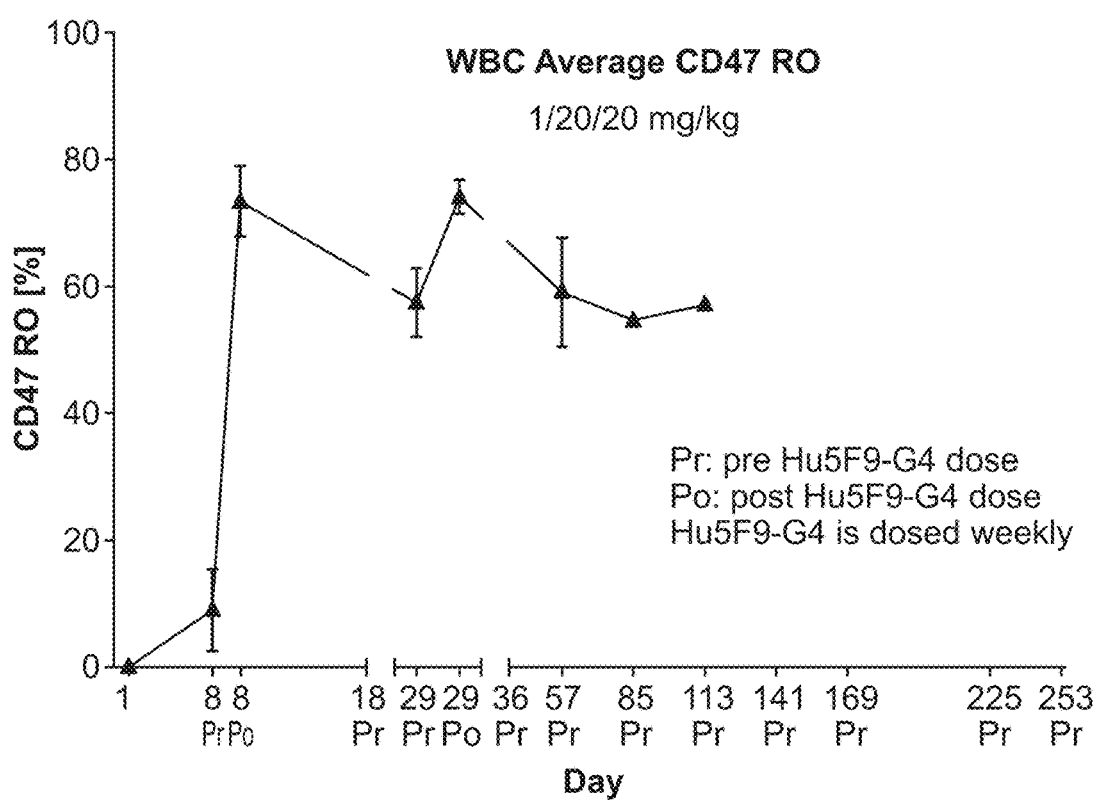

METHODS FOR DETERMINING AND ACHIEVING THERAPEUTICALLY EFFECTIVE DOSES OF ANTI-CD47 AGENTS IN TREATMENT OF CANCER

CROSS REFERENCE

This application is a Continuation and claims benefit of U.S. application Ser. No. 16/089,115, filed Sep. 27, 2018, which claims the benefit of PCT Application No. PCT/US2017/027662, filed Apr. 14, 2017, which claims benefit of U.S. Provisional Patent Application No. 62/323,330 filed Apr. 15, 2016, and U.S. Provisional Patent Application No. 62/427,679, filed Nov. 29, 2016, which applications are incorporated herein by reference in their entirety.

BACKGROUND

The large majority of cancers worldwide are solid tumors. In 2016, it is estimated that over 1,600,000 people will be newly diagnosed with a malignant solid tumor in the US (Siegel et al. (2016), Cancer statistics, 2016. CA: A Cancer Journal for Clinicians, 66:7-30). Current standards of care for solid tumors include surgical excision, radiotherapy, cytotoxic chemotherapy, and molecularly targeted small molecules and monoclonal antibodies (mAbs). Despite these therapies, most patients with metastatic cancer will die of the disease and/or treatment complications. Small molecules that target cancers have limited efficacy as single agents because of pre-existing or emergent resistance and usually exhibit toxicity to normal cells.

The development of therapeutic mAbs has substantially impacted treatment of some types of cancer. Conventionally these recombinant proteins specifically bind cancer cells and either block signaling pathways or mark them for destruction by the immune system. However, targeted mAbs exist for only a few cancers, even the most effective mAbs may require combination therapy with conventional chemotherapy, and often produce an incomplete therapeutic response. In many patients, the disease becomes resistant to mAb treatment by loss of the antibody target (when the molecule is not essential for tumor cell survival) or by developing resistance to tumor killing. Usually patients experience a relapse of their disease.

CD47 has been identified as a key molecule mediating cancer cell evasion of phagocytosis by the innate immune system. CD47 appears to be an indispensable means by which cancer cells, including cancer stem cells, overcome intrinsic expression of their prophagocytic, "eat me," signals. The progression from normal cell to cancer cell involves changes in genes and/or gene expression that trigger programmed cell death (PCD) and programmed cell removal (PCR). Many of the steps in cancer progression subvert the multiple mechanisms of PCD, and the expression of the dominant antiphagocytic signal, CD47, may represent an important checkpoint.

CD47 expression is increased on the surface of cancer cells from a large number of diverse human tumor types including the following primary malignancies: head and neck, melanoma, breast, lung, ovarian, pancreatic, colon, bladder, prostate, leiomyosarcoma, glioblastoma, medulloblastoma, oligodendroglioma, glioma, lymphoma, leukemia, and multiple myeloma. In murine xenograft studies, it has been shown that CD47-blocking antibodies inhibit human cancer growth and metastasis by enabling the phagocytosis and elimination of cancer stem cells and cancer cells from various hematologic malignancies and several solid tumors.

CD47 serves as the ligand for SIRPα, which is expressed on phagocytic cells including macrophages and dendritic cells. When SIRPα is activated by CD47 binding, it initiates a signal transduction cascade resulting in inhibition of phagocytosis. In this way, CD47 functions as an antiphagocytic signal by delivering a dominant inhibitory signal to phagocytic cells. It has been demonstrated that a blocking anti-CD47 mAb enabled the phagocytic elimination of cancer stem cells and cancer cells.

In mouse xenografts, CD47-blocking mAbs inhibit human xenograft tumor growth and metastasis by enabling the phagocytosis and elimination of cancer cells from various hematologic malignancies and solid tumors. Furthermore, CD47 blocking mAbs synergize with the established cancer cell targeting mAbs rituximab, trastuzumab, and cetuximab to enhance therapeutic efficacy in some tumor types.

Methods for effective delivery of antibodies that block CD47 interaction with SIRPα are of clinical interest, and are provided herein.

SUMMARY OF THE INVENTION

Methods are provided for treating an individual with a therapeutic dose of anti-CD47 agent. The methods of the invention administer effective priming and therapeutic doses of an agent that binds to CD47, which is present on cancer cells and which can be present on red blood cells (RBC). An anti-CD47 agent for use in the methods of the invention interferes with binding between CD47 present on a cancer cell to SIRPα present on a phagocytic cell. Generally both such cells are present in the individual being treated. Such methods, in the presence of a pro-phagocytic signal, can increase phagocytosis of the target cancer cell while reducing undesirable side effects on RBC populations.

The subject methods can be used to treat a subject for cancer with an agent that binds to CD47, including anti-CD47 antibodies, where the term antibodies encompasses antibody fragments and variants thereof, and SIRPα polypeptides, e.g, multivalent polypeptides comprising a SIRPα sequence. Suitable agents include, without limitation, Hu5F9, including Hu5F9-G4; CC-9002; TTI-621 and bivalent, tetravalent, etc. high affinity SIRPα polypeptides.

As has been previously described, a therapeutic dose of a CD47 binding agent can lead to a loss of erythrocytes (RBCs) and anemia. Administration of a priming dose of CD47 binding agent significantly reduces toxicity due to loss of older erythrocytes while sparing younger erythrocytes. Without being bound by theory, it is believed that the primer agent increases production of reticulocytes (younger RBC), which may be more resistant to CD47 mediated phagocytosis and therefore are less susceptible to loss during subsequent administration of the anti-CD47 agent. Methods are provided for determining an appropriate timing dose for preclinical or clinical use, by determining the receptor occupancy of CD47 of blood cells, e.g. RBC and WBC. It is shown herein that a suitable priming dose provides for greater than about 50% receptor occupancy on RBC. The methods of determining the priming dose can be applied to any CD47 binding agent.

In some embodiments of the invention, an effective priming dose of Hu-5F9G4 is provided, where the effective priming dose for a human is around about 1 mg/kg, e.g. from at least about 0.5 mg/kg up to not more than about 5 mg/kg; from at least about 0.75 mg/kg up to not more than about 1.25 mg/kg; from at least about 0.95 mg/kg up to not more than about 1.05 mg/kg; and may be around about 1 mg/kg.

An initial dose of a CD47 binding agent, including but not limited to a priming dose, may also lead to hemagglutination for a period of time immediately following infusion. Without being bound by the theory, it is believed that the initial dose of a multivalent CD47 binding agent may cause cross-linking of RBC bound to the agent. In certain embodiments of the invention, a CD47 binding agent is infused to a patient in an initial dose, and optionally in subsequent doses, over a period of time and/or concentration that reduces the possibility of hematologic microenvironments where there is a high local concentration of RBC and the agent.

In some embodiments of the invention, an initial dose of a CD47 binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In some embodiments a priming dose is fractionated into two or more subdoses, delivered over a period of time from about 1 day, about 2 days, about 3 days, about 4 days, about 1 week, about 10 days, about 2 weeks.

In other embodiments, an initial dose of a CD47 binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days.

In some embodiments a priming dose may be delivered through a sub-cutaneous route, by injection, patch, osmotic pump, and the like as known in the art.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent.

In some embodiments of the invention, the therapeutic (maintenance) dose is sufficient to achieve a circulating level of greater than 100 µg/ml for a sustained period of time. In some such embodiments the anti-CD47 agent is the antibody 5F9. In some embodiments the sustained period of time is up to about 1 week. In some embodiments the sustained period of time is up to about 10 days. In some embodiments the sustained period of time is up to about 2 weeks. In some embodiments the maintenance dose is from about 10 mg/kg to about 25 mg/ml, from about 12.5 mg/kg to about 22.5 mg/kg, from about 15 mg/kg to about 20 mg/kg, from about 17.5 mg/kg to about 20 mg/kg, from about 10 mg/kg to about 20 mg/kg. The maintenance dose may be administered at a periodicity that provides for sustained serum levels of greater than about 100 µg/ml, where administration may be weekly, every 8 days, every 9 days, every 10 days, every 11 days, every 12 days, every 13 days, every two weeks, every 3 weeks, and may provide for follow-up therapy of less frequent administration, e.g. monthly, semi-monthly, bi-monthly, etc.

In some embodiment a therapeutic regimen for treatment of cancer comprises administration of a loading dose an anti-CD47 antibody, including without limitation 5F9-G4, where the loading dose is administered twice weekly at a dose of from 10 mg/kg to 40 mg/kg; and may be administered twice weekly at a dose of from 20 mg/kg to 30 mg/kg. The patient is then administered a maintenance dose, weekly or semi-weekly, at a dose of from 10 mg/kg to 40 mg/kg; and may be at a dose of from 20 mg/kg to 30 mg/kg. In some such embodiments the cancer is a solid tumor. In some such embodiments the cancer is a hematologic cancer, e.g. a leukemia, including without limitation acute myeloid leukemia.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 3A-3C. WBC CD47 Receptor Occupancy Increases with Dose Concentration. The graphs depict receptor occupancy of CD47 on WBC at varying doses of antibody.

FIG. 8A. Representative peripheral smear micrographs taken from patients pre-treatment and 4 hours post first 1 mg/kg (priming) dose of Hu5F9-G4. Significant hemagglutination is observed in the 1 hour infusion which is significantly reduced in the 3 hour infusion. FIG. 8B. Extension of the priming dose infusion duration from 1 to 3 hours significantly reduces the frequency and severity of hemagglutination. 1+ to 3+ represents the percentage of agglutinated red blood cells observed on peripheral smear at 4 hours post-treatment. N=number of patients treated with each infusion time length.

DETAILED DESCRIPTION

Figure 1:
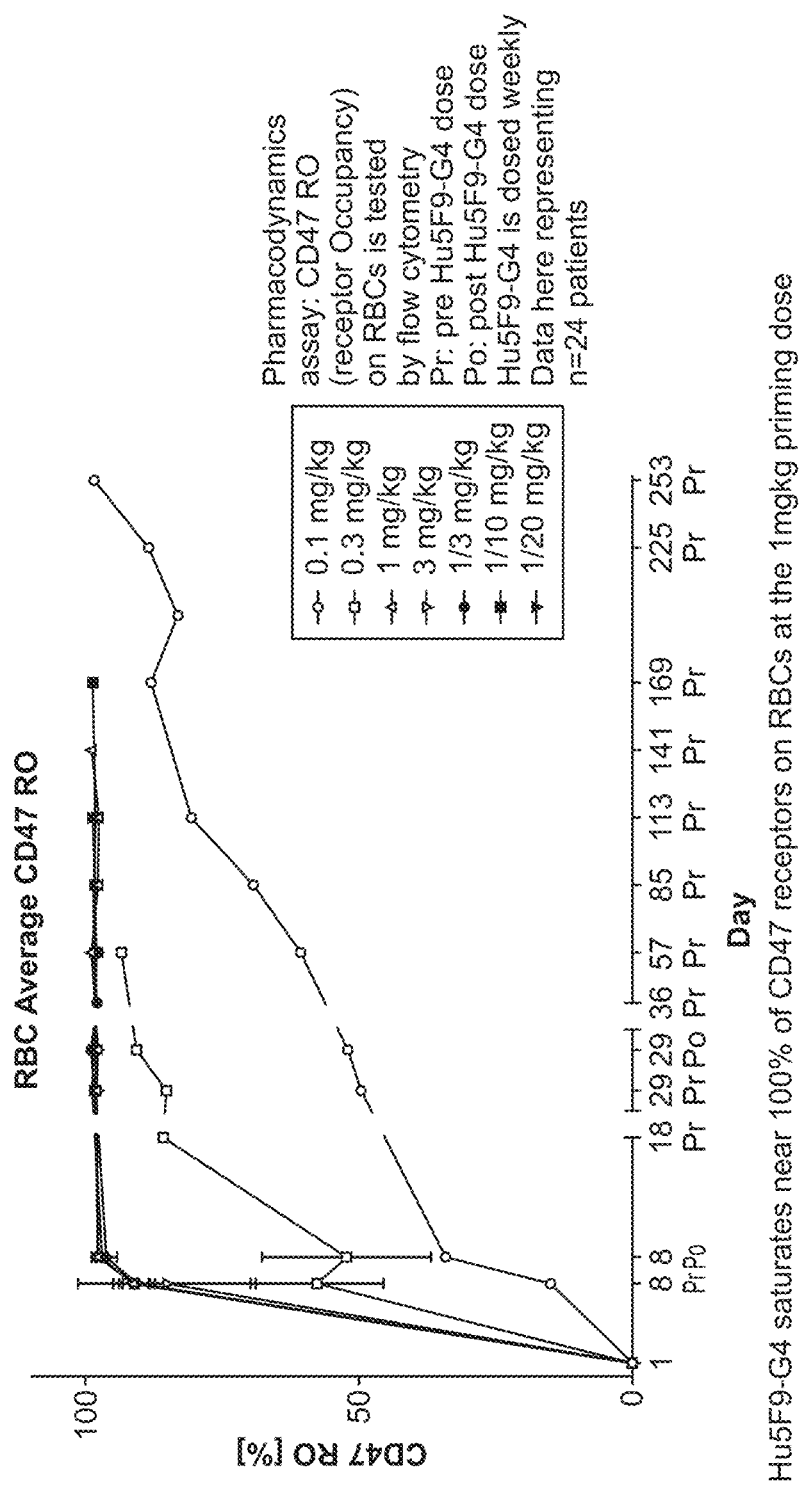
FIG. 1. Red Blood Cells are Saturated with Antibody at Low Doses. The graph depicts receptor occupancy of CD47 on RBC in patients dosed with Hu5F9-G4 at the dosage indicated. A dose of 1 mg/kg is sufficient to saturate RBC binding sites.

The present invention relates to methods of treating a subject with a therapeutic dose of anti-CD47 agent.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limit of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Anti-CD47 agent. As used herein, the term "anti-CD47 agent" refers to any agent that reduces the binding of CD47 (e.g., on a target cell) to SIRPα (e.g., on a phagocytic cell). For the specific methods of the present invention, agents that bind to CD47 are of interest. Non-limiting examples of suitable anti-CD47 reagents include SIRPα reagents, including without limitation high affinity SIRPα polypeptides and anti-CD47 antibodies or antibody fragments. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Clone CC-9002 is disclosed in WO2013119714, herein specifically incorporated by reference. Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. For the specific methods of the present invention, multivalent SIRPα polypeptides are of interest.

A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. A SIRPα agent of interest includes TTI-621, see clinical trial identifier NCT02663518, herein specifically incorporated by reference.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold at least 20-fold at least 50-fold at least 100-fold at least 500-fold or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.)

As used herein, a "target cell" is a cell expressing CD47 on the surface, where masking or otherwise altering the CD47 positive phenotype (e.g., by administration of an anti-CD47 agent) results in increased phagocytosis. Usually a target cell is a mammalian cell, for example a human cell.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of an anti-CD47 agent is an amount that is sufficient to palliate, ameliorate, stabilize, reverse, prevent, slow or delay the progression of the disease state (e.g., cancer) by increasing phagocytosis of a target cell (e.g., a target cell). Thus, a therapeutically effective dose of an anti-CD47 agent reduces the binding of CD47 on an target cell, to SIRPα on a phagocytic cell, at an effective dose for increasing the phagocytosis of the target cell.

In some embodiments, a therapeutically effective dose leads to sustained serum levels of anti-CD47 agent, i.e. trough levels (e.g., an anti-CD47 antibody) of about 40 µg/ml or more (e.g, about 50 µg/ml or more, about 60 µg/ml or more, about 75 µg/ml or more, about 100 µg/ml or more, about 125 µg/ml or more, or about 150 µg/ml or more). In some embodiments, a therapeutically effective dose leads to sustained serum levels of anti-CD47 agent (e.g., an anti-CD47 antibody) that range from about 40 µg/ml to about 300 µg/ml (e.g, from about 40 µg/ml to about 250 µg/ml, from about 40 µg/ml to about 200 µg/ml, from about 40 µg/ml to about 150 µg/ml, from about 40 µg/ml to about 100 µg/ml, from about 50 µg/ml to about 300 µg/ml, from about 50 µg/ml to about 250 µg/ml, from about 50 µg/ml to about 200 µg/ml, from about 50 µg/ml to about 150 µg/ml, from about 75 µg/ml to about 300 µg/ml from about 75 µg/ml to about 250 µg/ml, from about 75 µg/ml to about 200 µg/ml, from about 75 µg/ml to about 150 µg/ml, from about 100 µg/ml to about 300 µg/ml, from about 100 µg/ml to about 250 µg/ml, or from about 100 µg/ml to about 200 µg/ml). In some embodiments, a therapeutically effective dose for treating solid tumors leads to sustained serum levels of anti-CD47 agent (e.g., an anti-CD47 antibody) of about 100 µg/ml or more, e.g., sustained serum levels that range from about 100 µg/ml to about 500 µg/ml, from about 100 µg/ml to about 400 µg/ml, from about 100 µg/ml to about 300 µg/ml, from about 100 µg/ml to about 200 µg/ml.

Accordingly, series of therapeutically effective doses would be able to achieve and maintain a serum level of anti-CD47 agent. A therapeutically effective dose of an anti-CD47 agent can depend on the specific agent used, but is usually about 5 mg/kg body weight or more (e.g., about 8 mg/kg or more, about 10 mg/kg or more, about 15 mg/kg or more, about 20 mg/kg or more, about 25 mg/kg or more, about 30 mg/kg or more, about 35 mg/kg or more, or about 40 mg/kg or more), or from about 10 mg/kg to about 40 mg/kg (e.g., from about 10 mg/kg to about 35 mg/kg, or from about 10 mg/kg to about 30 mg/kg). The dose required to achieve and/or maintain a particular serum level is proportional to the amount of time between doses and inversely proportional to the number of doses administered. Thus, as the frequency of dosing increases, the required dose decreases. The optimization of dosing strategies will be readily understood and practiced by one of ordinary skill in the art.

In some embodiments, a priming dose is defined a dose (i.e., an amount) that is sufficient to cause compensatory reticulocytosis, without undue anemia. In some embodiments a priming dose is defined as a dose that causes an anemia that is not worsened by subsequent doses. A priming dose of an anti-CD47 agent can depend on the specific agent used, but is generally from about 0.5 to about 5 mg/kg.

The term "priming dose" or as used herein refers to a dose of an anti-CD47 agent that primes a subject for administration of a therapeutically effective dose of anti-CD47 agent such that the therapeutically effective dose does not result in a severe loss of RBCs (reduced hematocrit or reduced hemoglobin). The specific appropriate priming dose of an anti-CD47 agent can vary depending on the nature of the agent used and on numerous subject-specific factors (e.g., age, weight, etc.). Examples of suitable priming doses of an anti-CD47 agent include from about 0.5 mg/kg to about 5 mg/kg, from about 0.5 mg/kg to about 4 mg/kg, from about 0.5 mg/kg to about 3 mg/kg, from about 1 mg/kg to about 5 mg/kg, from about 1 mg/kg to about 4 mg/kg, from about 1 mg/kg to about 3 mg/kg, about 1 mg/kg, about 2 mg/kg, about 3 mg/kg, about 4 mg/kg, about 5 mg/kg.

A "maintenance dose" is a dose intended to be a therapeutically effective dose. For example, in experiments to determine the therapeutically effective dose, multiple different maintenance doses may be administered to different subjects. As such, some of the maintenance doses may be therapeutically effective doses and others may be sub-therapeutic doses.

A "loading dose" may be used to achieve a therapeutic level of antibody before switching to a maintenance dose. A loading dose can be the same be the same or higher or lower than the maintenance dose, but will generally provide for a higher overall delivery of the agent over a given period of time. For example, a loading dose can be the same or lower than a maintenance dose, but delivered more frequently, e.g. daily, every other day, every third day, twice weekly, weekly, and the like. Alternatively a loading dose can be a higher dose than a maintenance dose, and delivered at the same periodicity, or more frequently, e.g. daily, every other day, every third day, twice weekly, weekly, and the like.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, or binding of a SIRPα polypeptide). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-8}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member). Suitable specific binding members include agents that specifically bind CD47 and/or SIRPα (i.e., anti-CD47 agents), or that otherwise block the interaction between CD47 and SIRPα.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The terms "phagocytic cells" and "phagocytes" are used interchangeably herein to refer to a cell that is capable of phagocytosis. There are three main categories of phagocytes: macrophages, mononuclear cells (histiocytes and monocytes); polymorphonuclear leukocytes (neutrophils) and dendritic cells.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample comprising target cells or normal control cells or suspected of comprising such cells or biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Methods

Receptor occupancy (RO) assay measures the level of CD47 occupancy by CD47 binding agents, e.g. anti-CD47 antibody (Ab). The purpose of measuring the level of CD47 RO is to determine the relationship between the dose of a CD47 binding agent, the CD47 receptor saturation, and pharmacologic effect. The percent of receptor occupancy over time may provide useful information regarding the amount of drug or duration of exposure needed to produce the desired pharmacological effect. This assay can be used to determine the overall RO in the body by measuring the CD47 RO on surrogate cells, e.g. on CD45 negative (−) red blood cells (RBCs) and CD45 positive (+) white blood cells (WBCs), or other cell populations, e.g. bone marrow or tissue cells obtained through tissue biopsies. The RO assay can also be used to determine CD47 RO on target cells, e.g. RBC, leukemia cells or solid tumor cells, for CD47 binding and or blocking therapies.

Of interest is the use of this assay to determine the threshold of CD47 receptor occupancy that is correlated with the desired pharmacological effect. This threshold can be determined by assays performed ex vivo (in vitro) or by analysis of samples during in vivo dosing/treatment.

In one embodiment of the assay, a CD47 binding standard curve on a cell of interest cells is made by using fluorochrome-conjugated antibody at various concentrations. Receptor occupancy is measured by incubating the target cells with unlabeled antibody under different concentrations, and then the cells were either assayed in in vitro phagocytosis or incubated with a saturating concentration of labeled antibody based on the standard curve and analyzed for binding by flow cytometry. Receptor occupancy was calculated as follows:

$$\% \text{ RO} = 100 - ((\text{MFI}_{test} - \text{MFI}_{unstained}) / (\text{MFI}_{saturated\ STD} - \text{MFI}_{unstained})) \times 100$$

In other embodiments the assay is performed by infusing a patient with a defined dose of antibody, obtaining a tissue sample, e.g. a blood sample, from the patient, usually before and after infusion of the antibody. The tissue sample is incubated with a saturating concentration of labeled antibody, and analyzed by flow cytometry. The analysis may be gated, for example, on red blood cells, white blood cells, cancer cells, etc.

It has been found that a priming dose that achieves at least about 80% saturation of CD47 on RBC is sufficient to induce compensation for anemia and reduce degree of anemia on subsequent doses. In humans, the priming dose has been found to be as discussed above, i.e. from about 0.5 mg/kg to about 5 mg/kg. In some embodiments of the invention, a receptor occupancy assay is performed with a candidate CD47 bind agent to determine the level of priming dose that provides for at least about 50% saturation on RBC, at least about 60% saturation, at least about 70% saturation, at least about 80% saturation, at least about 90% saturation, at least about 95% saturation, at least about 99% saturation, or more.

In some embodiments of the invention, a receptor occupancy assay is performed to determine the appropriate priming dose for a candidate anti-CD47 agent, e.g. an antibody that binds to CD47, a SIRPα polypeptide, etc.

Treatment Methods

Methods are provided for treating a subject with a therapeutic dose of anti-CD47 agent. The subject methods include a step of administering a primer agent to subject, followed by a step of administering a therapeutically effective dose of an anti-CD47 agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

The administration of a therapeutically effective dose of an anti-CD47 agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of 5 mg/kg), and each subsequent dose can be increased by a particular increment (e.g., by 5 mg/kg), or by variable increments, until a therapeutic dose (e.g., 30 mg/kg) is reached, at which point administration may cease or may continue (e.g., continued therapeutic doses, e.g., doses of 30 mg/kg). As another non-limiting example to illustrate escalating concentration (i.e., increasing doses), a therapeutically effective dose can be administered weekly, beginning with a therapeutic dose (e.g., a dose of 10 mg/kg), and each subsequent dose can be increased by a particular increment (e.g., by 10 mg/kg), or by variable increments, until a therapeutic dose (e.g., 30 mg/kg, 100 mg/ml, etc.) is reached, at which point administration may cease or may continue (e.g., continued therapeutic doses, e.g., doses of 30 mg/kg, 100 mg/ml, etc.). In some embodiments, administration of a therapeutically effective dose can be a continuous infusion and the dose can altered (e.g., escalated) over time.

Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., s.c., and the like.

Effective administration of primer agent. An initial dose of a CD47 binding agent, including but not limited to a priming dose, may lead to hemagglutination for a period of time immediately following infusion. Without being bound by the theory, it is believed that the initial dose of a multivalent CD47 binding agent may cause cross-linking of RBC bound to the agent. In certain embodiments of the invention, a CD47 binding agent is infused to a patient in an initial dose, and optionally in subsequent doses, over a period of time and/or concentration that reduces the possibility of hematologic microenvironments where there is a high local concentration of RBC and the agent.

In some embodiments of the invention, an initial dose of a CD47 binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In other embodiments, an initial dose of a CD47 binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent. There is reduced hemagglutination after the priming dose, and therefore the extended infusion time is not required.

Kits

Also provided are kits for use in the methods. The subject kits include a primer agent and an anti-CD47 agent. In some embodiments, a kit comprises two or more primer agents. In some embodiments, a kit comprises two or more anti-CD47 agents. In some embodiments, a primer agent is provided in a dosage form (e.g., a priming dosage form). In some embodiments, a primer agent is provided in two or more different dosage forms (e.g., two or more different priming dosage forms). In some embodiments, an anti-CD47 agent is provided in a dosage form (e.g., a therapeutically effective dosage form). In some embodiments, an anti-CD47 agent is provided in two or more different dosage forms (e.g., two or more different therapeutically effective dosage forms). In the context of a kit, a primer agent and/or an anti-CD47 agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility. The subject methods and kits can be used to treat any infliction where the target cells exhibit an increased expression of CD47 relative to normal cells of the same type. The anti-CD47 agent that is administered inhibits the interaction between SIRPα (e.g., on a phagocyte) and CD47 on an target cell (e.g., on a cancer cell, on an infected cell, etc.), thereby increasing in vivo phagocytosis of the target cell. Subject methods include administering to a subject in need of treatment a therapeutically effective dose of an anti-CD47 agent, including without limitation combinations of the reagent with another drug (e.g., an anti-cancer drug, etc.).

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

Cancers and cancer cells that can be treated include, but are not limited to, hematological cancers, including leukemia, lymphoma and myeloma, and solid cancers, including for example tumors of the brain (glioblastomas, medulloblastoma, astrocytoma, oligodendroglioma, ependymomas), carcinomas, e.g. carcinoma of the lung, liver, thyroid, bone, adrenal, spleen, kidney, lymph node, small intestine, pancreas, colon, stomach, breast, endometrium, prostate, testicle, ovary, skin, head and neck, and esophagus.

In an embodiment, the cancer is a hematological cancer. In an embodiment, the hematological cancer is a leukemia. In another embodiment, the hematological cancer is a myeloma. In an embodiment, the hematological cancer is a lymphoma.

In an embodiment, the leukemia is selected from acute myeloid leukemia (AML), acute lymphocytic leukemia (ALL), chronic lymphocytic leukemia (CLL) and chronic myelogenous leukemia (CML). In an embodiment, the leukemia is AML. In an embodiment, the leukemia is ALL. In an embodiment, the leukemia is CLL. In a further embodiment, the leukemia is CML. In an embodiment, the cancer cell is a leukemic cell, for example, but not limited to, an AML cell, an ALL cell, a CLL cell or a CML cell.

Suitable cancers responsive to treatment using an anti-CD47 agent include without limitation leukemia; acute myeloid leukemia (AML); acute lymphoblastic leukemia (ALL); metastasis; minimal residual disease; solid tumor cancers, e.g., breast, bladder, colon, ovarian, glioblastoma, leiomyosarcoma, and head & neck squamous cell carcinomas; etc. For examples, see: (i) Willingham et al., Proc Natl Acad Sci USA. 2012 Apr. 24; 109(17):6662-7: "The CD47-signal regulatory protein alpha (SIRPa) interaction is a therapeutic target for human solid tumors"; (ii) Edris et al., Proc Natl Acad Sci USA. 2012 Apr. 24; 109(17):6656-61: "Antibody therapy targeting the CD47 protein is effective in a model of aggressive metastatic leiomyosarcoma"; and (iii) US patent application 20110014119; all of which are herein incorporated in their entirety.

Pharmaceutical Compositions. Suitable anti-CD47 agents and/or primer agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an anti-CD47 agent or primer agent includes use in combination with another therapeutic agent (e.g., another anti-infection agent or another anti-cancer agent). Therapeutic formulations comprising one or more anti-CD47 agents and/or primer agents of the invention are prepared for storage by mixing the anti-CD47 agent or primer agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The anti-CD47 agent or primer agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

An anti-CD47 agent or primer agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the anti-CD47 agents and/or primer agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing a therapeutic dosage range and/or a priming dosage range for use in humans. The exact formulation, route of administration and dosage can be chosen by the individual physician in view of the patient's condition.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Assay for Receptor Occupancy and Determination of Effective Dosage

Hu5F9-G4 serum concentrations between 50-250 µg/ml correlate with therapeutic efficacy in AML and solid tumors in xenograft mouse models. Twice weekly maintenance doses of 10 mg/kg achieve Hu5F9-G4 serum concentrations in the potentially therapeutic range in non-human primates. Weekly maintenance doses of 10 mg/kg achieve Hu5F9-G4 serum concentrations in the potentially therapeutic range in patients.

Receptor occupancy was measured by incubating the target cells with unlabeled Hu5F9-G4 under different concentrations, and then the cells were either assayed in in vitro phagocytosis or incubated with a saturating concentration of AF488-Hu5F9-G4 based on the standard curve and analyzed for binding by flow cytometry, gated on APC/FITC double population, and calculated MFI for each sample.

Receptor Occupancy $$\% \text{ RO} = 100 - ((MFI_{test} - MFI_{unstained}) / (MFI_{saturated\ STD} - MFI_{unstained})) \times 100$$

We first assessed Hu5F9-G4 administered to cynomolgus monkeys as a single intravenous infusion at 0, 0.1, 0.3, 1, 3, 10, and 30 mg/kg in separate individuals. All animals were evaluated for changes in clinical signs, food consumption, body weights, and clinical pathology parameters. Administration of Hu5F9-G4 was generally well tolerated, and no treatment-related effects were noted on a comprehensive list of clinical observations, food consumption, body weights, or clinical chemistry parameters indicative of renal, hepatic, or cardiac effects. Clinical hematology assessment indicated that Hu5F9-G4 caused a dose-dependent anemia associated with reticulocytosis and spherocytosis in all animals. The nadir of the anemia occurred approximately 5-7 days after the infusion and generally correlated with dose. The severity of the anemia was variable as the two animals administered 30 mg/kg exhibited different responses. Importantly, in all animals the anemia spontaneously resolved, returning to baseline levels after approximately two weeks. In all cases, no free plasma hemoglobin was detected, indicating the absence of intravascular hemolysis. No other abnormalities of white blood cells or platelets were observed. Thus, consistent with its known function in regulating RBC phagocytosis, Hu5F9-G4 caused a transient anemia, likely due to erythrophagocytosis, but was otherwise well-tolerated.

With single-dose administration of Hu5F9-G4, pharmacokinetic data demonstrated that only the 10 and 30 mg/kg dose levels were able to transiently achieve serum levels in the range associated with efficacy in xenograft studies. This is likely due to the large antigen sink of CD47 expressed on circulating red and white blood cells, in addition to other non-hematopoietic tissues. Based on the previously described role of CD47 in the normal clearance of aging red blood cells, the Hu5F9-G4-related anemia observed in this study was considered related to the pharmacological action of Hu5F9-G4 binding to CD47 expressed on RBCs. The premature loss of RBCs was compensated by an ensuing reticulocytosis, and over time, the initial anemia resolved with replacement by younger cells.

From these considerations, we conducted a separate dose-escalation study in NHP based on the hypothesis that initial low doses would blunt the loss of RBC and stimulate production of less-susceptible young RBC, thereby facilitating tolerance of subsequent larger doses. Two animals were enrolled into this study and dosed at one-week intervals: one with EPO pre-treatment (3, 10, 30, 100, and 300 mg/kg), and one with no pre-treatment (1, 3, 10, 30, and 100 mg/kg). In both cases, the NHP exhibited a mild anemia with initial dosing that did not worsen with repeated administrations. In fact, the hemoglobin only reached the upper threshold for transfusion in humans, even without EPO pretreatment. Strikingly, the animals tolerated all doses well, including 100 and 300 mg/kg, with no additional blood or metabolic abnormalities. At the end of the study, both animals were euthanized, and necropsy and histopathology analysis revealed no abnormalities.

From this dose-escalation study, we determined the pharmacokinetics of Hu5F9-G4 in NHP. Consistent with the presence of a large antigen sink of CD47 expressed by normal tissues, the initial low doses of Hu5F9-G4 were rapidly cleared from the serum. In contrast, the higher doses of Hu5F9-G4 produced sustained serum levels indicating saturation of the antigen sink. Remarkably, the animal dosed at 300 mg/kg had a peak level of 5 mg/ml with a sustained level of more than 1 mg/ml for at least 2 weeks. These data, suggest that a priming dose followed by a larger maintenance dose regimen should be capable of achieving the sustained 50-250 µg/ml serum level that was associated with potent efficacy in the pre-clinical xenograft models.

These results led us to conduct another NHP pilot study using a priming-maintenance dosing approach to model potential clinical dosing strategies. The goal of the priming dose would be to stimulate production of young RBCs that would then facilitate larger maintenance doses capable of achieving sustained serum levels. We conducted a study in cynomolgus monkeys in which a priming dose (PD) of either 1 or 3 mg/kg was administered on Day 1, followed one week later by weekly maintenance dosing (MD) of 30 mg/kg for six weeks. All animals were evaluated for changes in clinical observations, food consumption, body weights, and clinical pathology parameters. No mortalities or changes in key clinical chemistry parameters indicative of renal, hepatic, or cardiac effects were noted. Administration of Hu5F9-G4 was well tolerated over the entire dosing course. In both cases, the priming dose resulted in mild anemia and reticulocytosis. As hypothesized, the maintenance doses were well-tolerated with no further declines in hemoglobin throughout the treatment course. By the end of the study, hemoglobin levels returned to the normal range. Pharmacokinetic analysis indicated that exposure to Hu5F9-G4 as measured by $C_{max}$ and the area under the serum concentration curve ($AUC_{0-43}$) in both animals achieved sustained serum Hu5F9-G4 levels within or above the potential therapeutic range for the duration of the maintenance dosing period with prolonged half-life after the final dose. These results suggest that PD1/MD30 or PD3/MD30 dosing strategies saturate the CD47 antigen sink. Collectively, these cynomolgus monkey studies demonstrated that a low priming dose of Hu5F9-G4 results in a modest anemia and compensatory reticulocytosis response that enabled subsequent higher maintenance doses of drug to be well tolerated.

A CD47 binding standard curve on human patients following treatment with a varying priming dose of Hu5F9-G4 was made by using AF488-conjugated Hu5F9-G4, as shown in FIG. 1. It can be seen that a priming dose of 1 mg/kg or more was able to saturate greater than 80% of the CD47 molecules on red blood cells with the first dose in patients, and prevents RBC agglutination with subsequent doses. Dose concentrations are shown, whereby ⅓ and 1/10 represents a first priming dose of 1 mg/kg followed by 3 mg/kg maintenance doses and a first priming dose of 1 mg/kg followed by 10 mg/kg maintenance doses, respectively.

Figure 2:
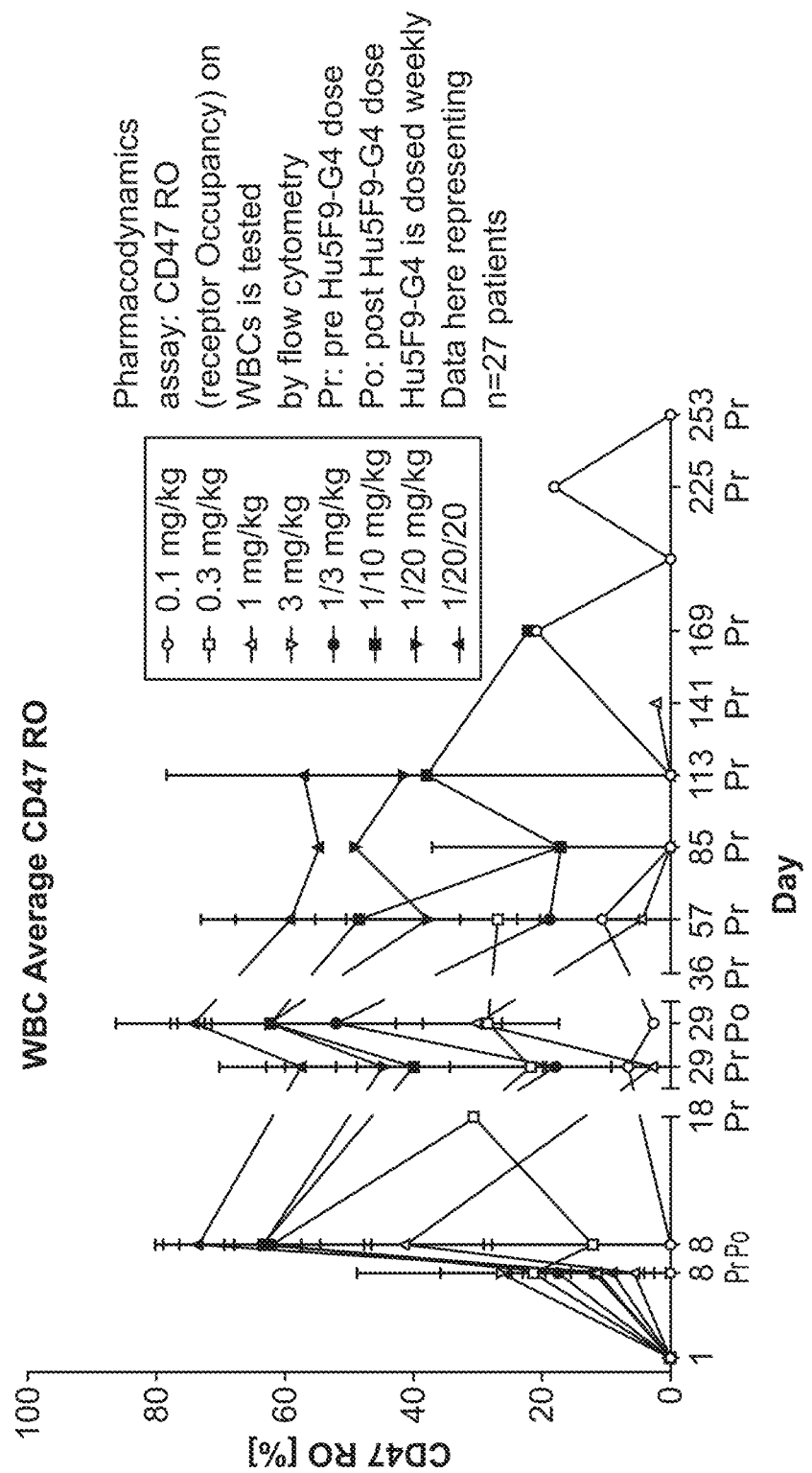
FIG. 2. WBC CD47 Receptor Occupancy Increases with Dose Concentration. The graph depicts receptor occupancy of CD47 on WBC in patients dosed with Hu5F9-G4 at the dosage indicated.
Figure 3A:
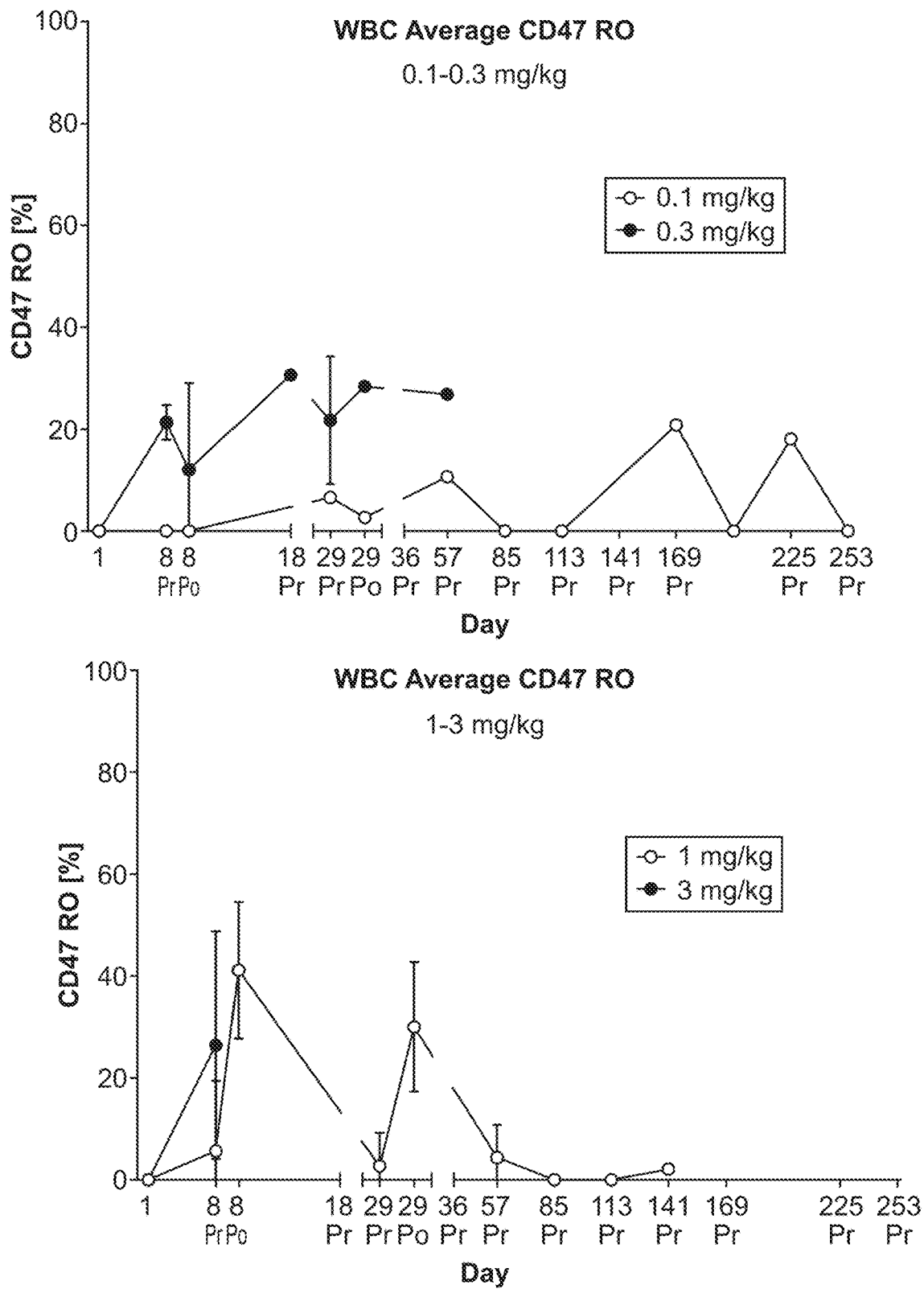

Shown in FIGS. 2 and 3 is the receptor occupancy results with different patients, showing the effect of increasing dose, and the saturation of receptors on white blood cells of human patients. Each line corresponds to a different patient. Dose concentrations are shown, whereby ⅓ and 1/10 represents a first priming dose of 1 mg/kg followed by 3 mg/kg maintenance doses and a first priming dose of 1 mg/kg followed by 10 mg/kg maintenance doses, respectively.

Figure 4:
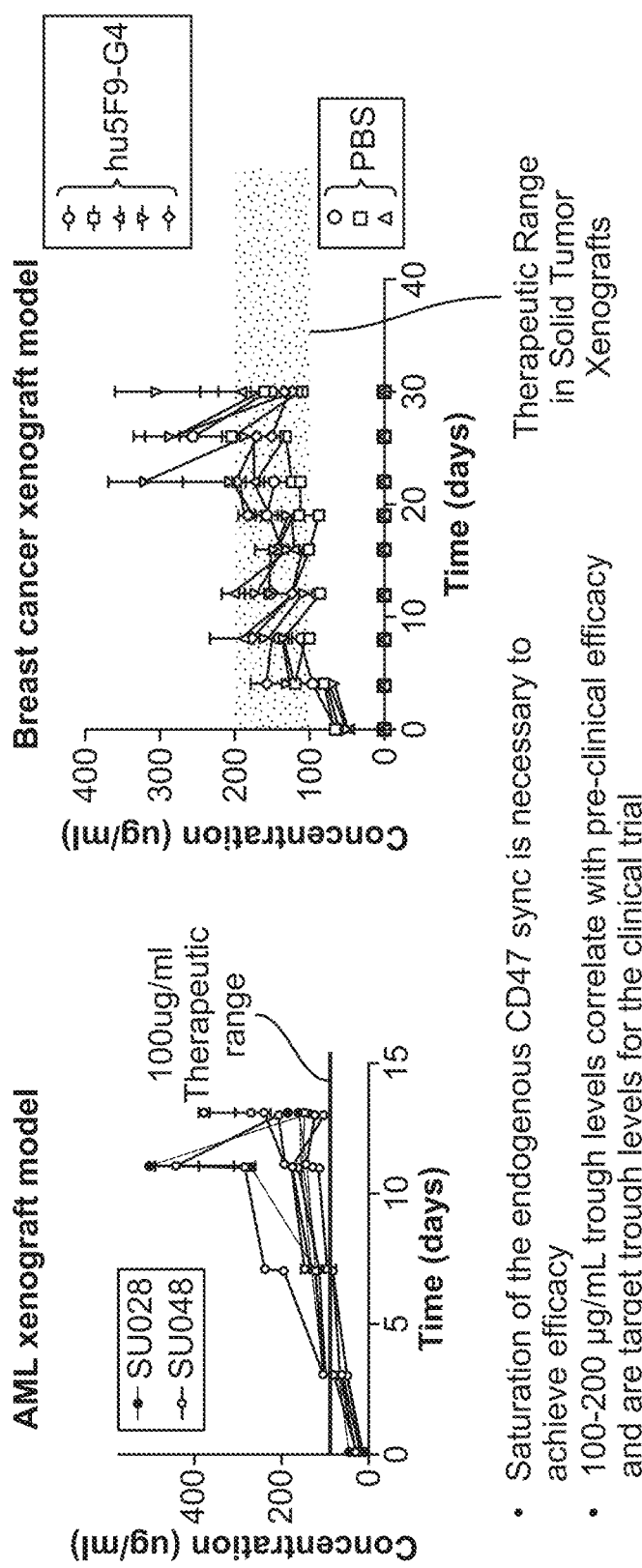
FIG. 4 provides graphs showing target trough levels of anti-CD47 antibody for clinical use.

Shown in FIG. 4, in a pre-clinical xenograft mouse model, 100-200 μg/ml trough levels are the therapeutic range, with saturation of the endogenous CD47 sink. These trough levels correlated with therapeutic anti-tumor efficacy. In a non-human primate (NHP) preclinical model, following the priming dose, target trough levels of 100 μg/ml were achieved in the 10 mg/kg cohort. The pharmacokinetic profiles are predictive of clinical pharmacokinetics.

Figure 5:
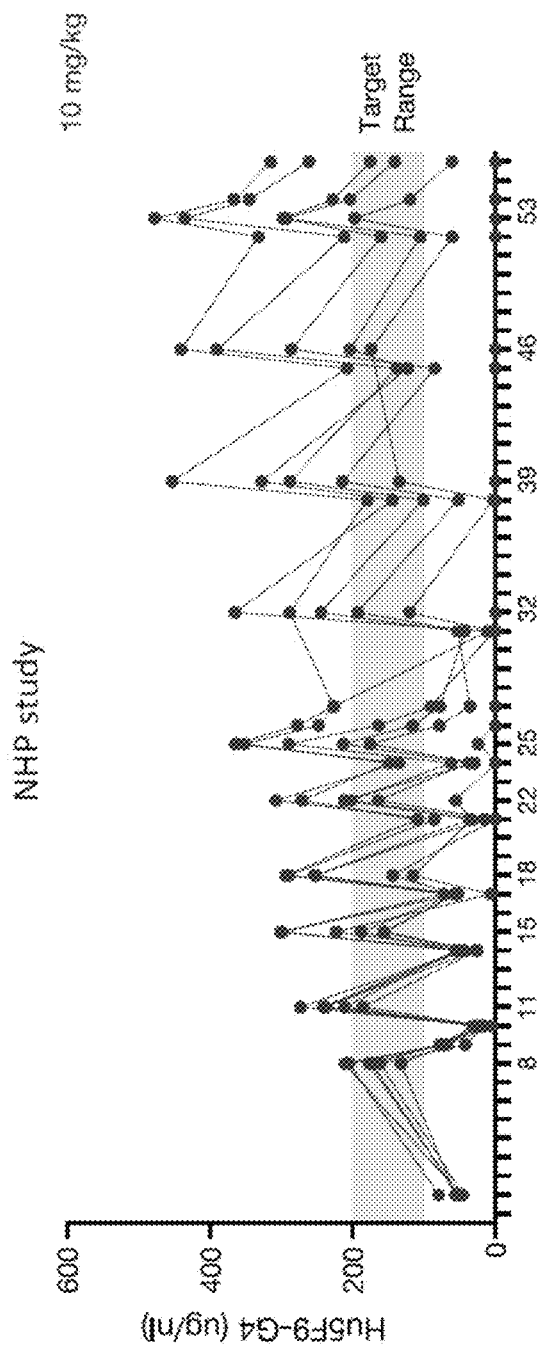
FIG. 5 is a graph showing pharmacokinetics of target trough levels of anti-CD47 antibody.
Figure 6:
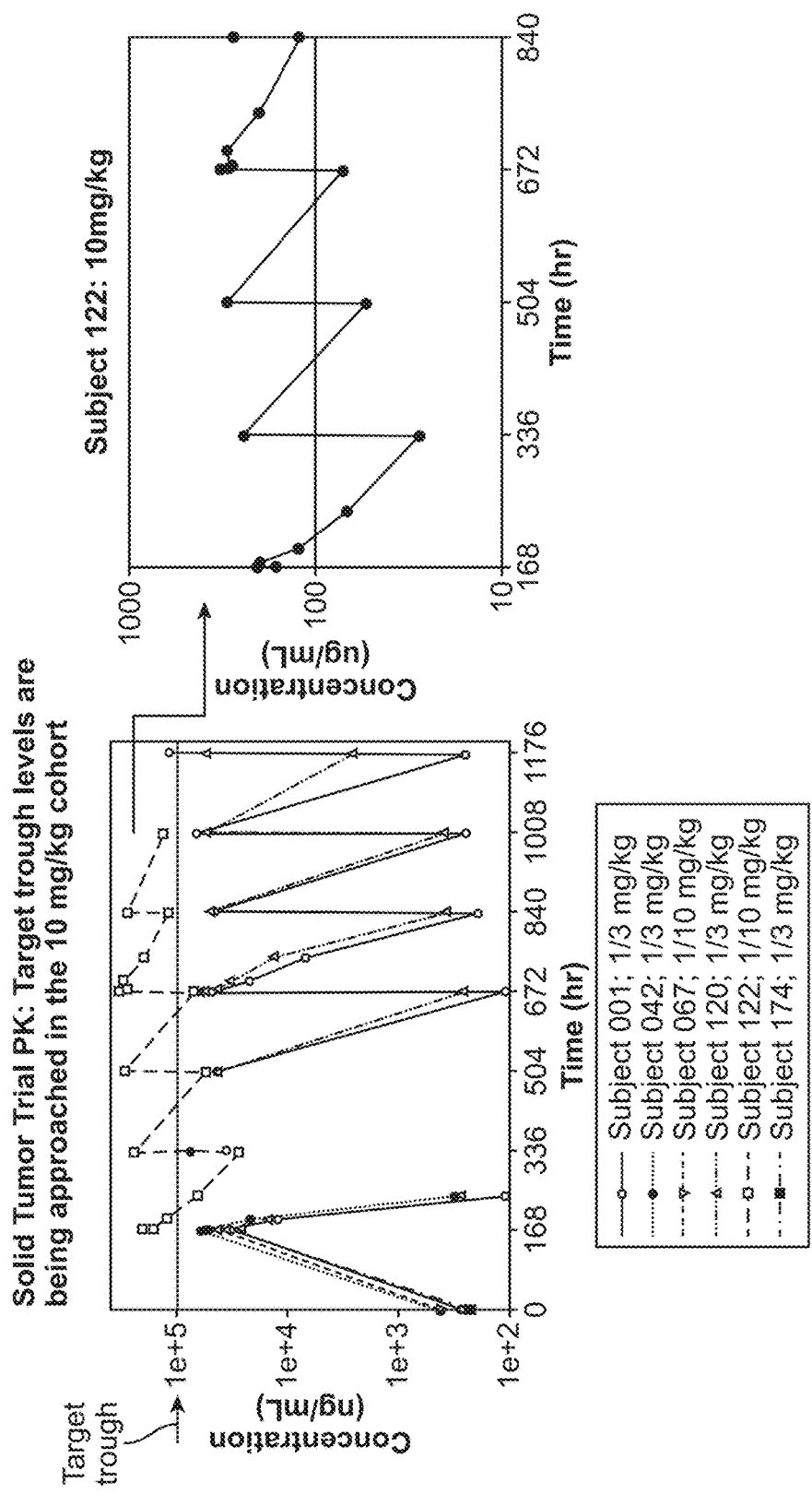
FIG. 6 is a graph showing that target trough levels are approached with repeated dosing at 10 mg/kg in human patients.

With weekly administration of a dose at 10 mg/kg in a human solid tumor patient the target trough of 100 μg/kg is achieved, illustrating the predictive power of the preclinical NHP model, when appropriately converted using FDA guidelines. In non-human primates dosing is twice weekly at 10 mg/kg (FIG. 5) and in humans dosing is 10 mg/kg weekly (FIG. 6).

Figure 7:
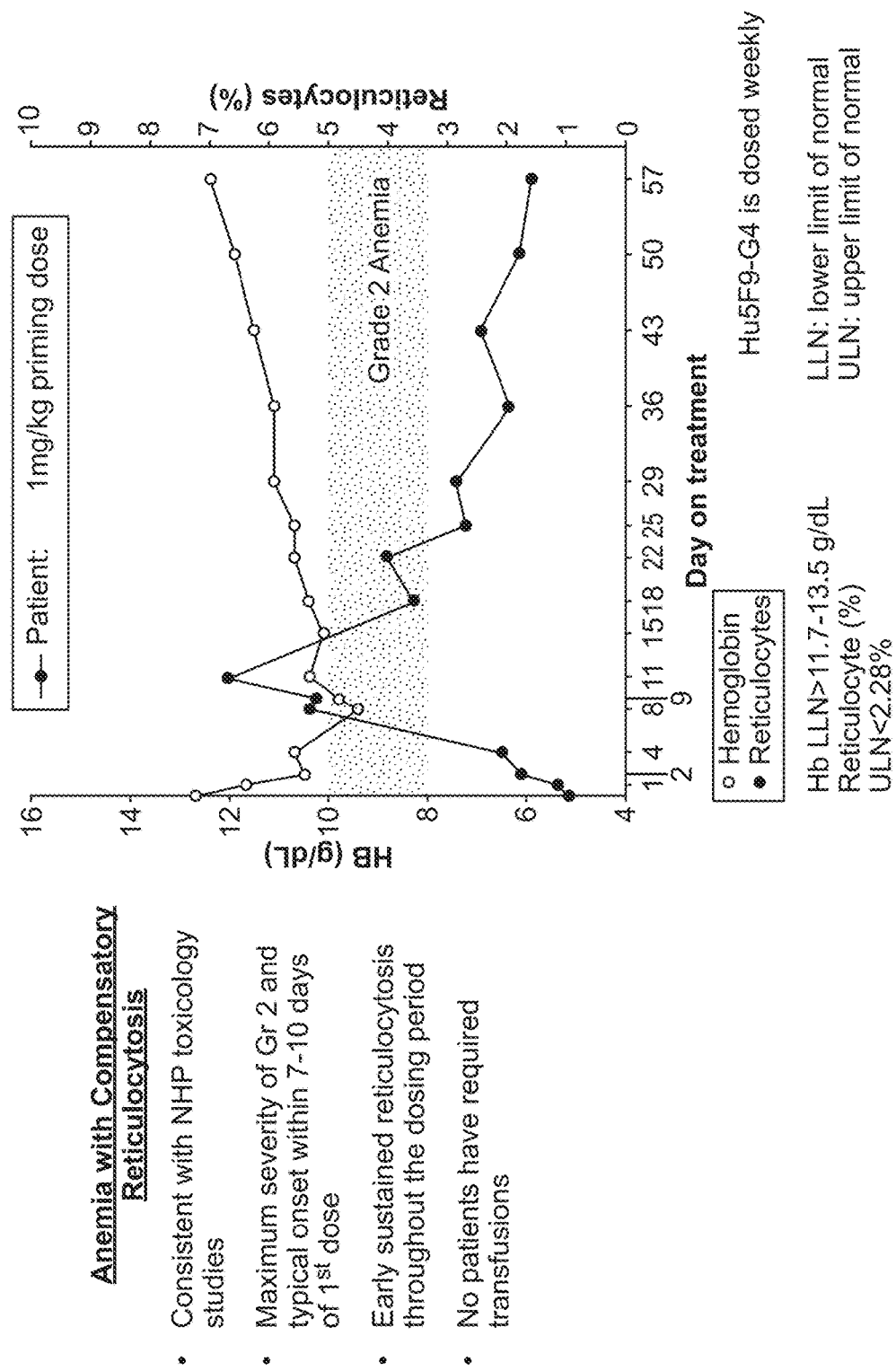
FIG. 7 is a graph showing anemia with compensatory reticulocytosis following administration of anti-CD47 antibody.

Initial anemia associated with administration of the anti-CD47 antibody has compensatory reticulocytosis. Shown in FIG. 7, there is an increase in the % of reticulocytes during weekly administration of Hu5F9-G4 in a human patient that is mainly seen after the first (priming) dose. Hu5F9-G4 is administered weekly.

Example 2

Reduction of Hemagglutination with Extended Infusion Time

Erythrocytes express CD47 on the cell surface. However aged erythrocytes lose CD47 cell surface expression and gain expression of prophagocytic signals. The loss or blockade of CD47 on the cell surface coupled with gain of prophagocytic signals leads to phagocytic clearance of erythrocytes. As discussed in Example 1, over a period of time from several days to several weeks, administration of a priming dose of anti-CD47 antibody can compensate for an initial transient anemia caused by administration of the anti-CD47 antibody by clearing aged erythrocytes and inducing reticulocytosis, where the blood population of red blood cells shifts to younger cells that express CD47 but do not have prophagocytic signals.

In addition to the extended effect of anemia and compensation, there can be an acute effect of hemagglutination immediately after administration of an anti-CD47 antibody. Without being bound by the theory, this may be attributed to very short term high concentrations of antibody and RBC localized at the site of administration, until normal blood flow dynamics distribute the cells and antibodies more equally. At high concentrations the antibody may bind to different RBC, thereby causing an undesirable cross-linking effect.

Figure 8B:
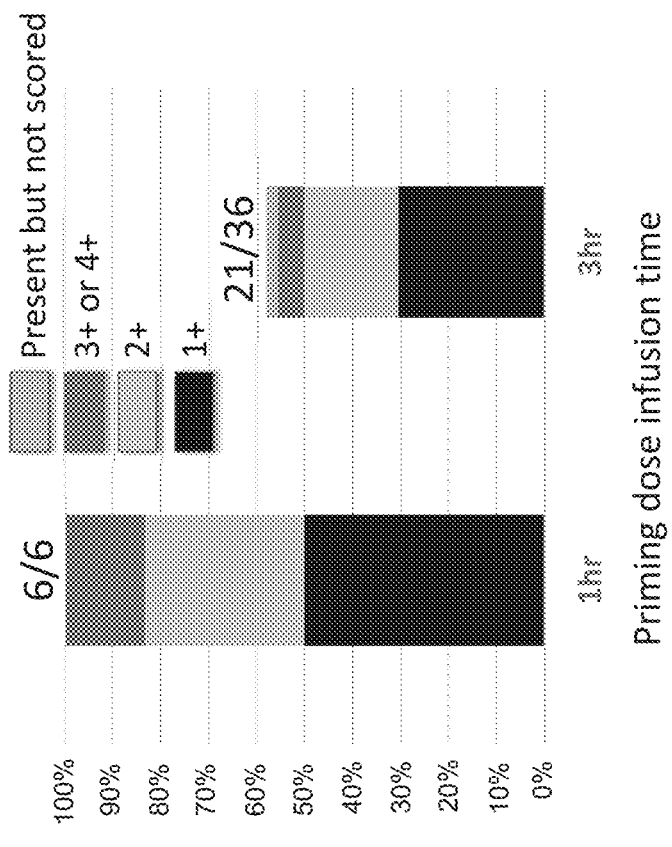
FIG. 8A-8B. Hemagglutination is mitigated with a prolonged infusion time of the priming dose. shows peripheral smear micrographs and graphs for hemagglutination associated with an initial infusion of an anti-CD47 antibody.
Figure 8A:
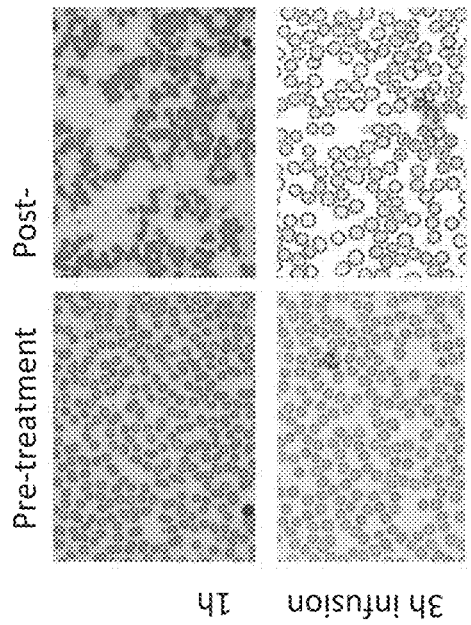

To reduce acute hemagglutination it is therefore desirable to administer the antibody in a manner that reduces the immediate concentration at the infusion site to levels where RBC are not cross-linked. In the initial protocols, a priming dose of antibody was administered in volumes of 250 ml. for doses of 0.1 mg/kg and 0.3 mg/kg; and in a volume of 500 ml. for a dose of 1 mg/kg. over a period of one hour. As shown in FIG. 8, this protocol can result in undesirable hemagglutination.

In contrast, when the same dose and concentration of antibody is administered to a patient over a period of 3 hours, there is a remarkable improvement in the level of agglutination, shown in FIG. 8. The extended administration can be performed for therapeutic dosing, after completion of priming, but is not required as there is a reduction in aged RBCs expressing prophagocytic signals after completion of the priming dose.

Example 3

Clinical Trial Protocol

A novel therapeutic mAb specifically binds CD47 and blocks it from interacting with its ligand, signal regulatory protein alpha (SIRPα), on phagocytic cells. This results in the phagocytosis and elimination of cancer cells via prophagocytic signals, which may include phosphatidylserine, calreticulin, and others. With the exception of red blood cells, normal cells generally do not express prophagocytic signals and are unaffected by the anti-CD47 mAb. The humanized CD47 blocking mAb, Hu5F9-G4, has been developed for clinical testing and has been administered safely at potentially therapeutic serum levels to non-human primates (NHPs). Nonclinical toxicology studies were conducted in NHPs (cynomolgus and rhesus monkeys) to support intravenous administration of Hu5F9-G4 in the clinical setting. Based on the data from the GLP 8-week toxicology study conducted in cynomolgus monkeys, the estimated safe starting dose for human trials is 0.1 mg/kg.

The pharmacokinetics (PK) and toxicokinetics (TK) of Hu5F9-G4 have been studied in the cynomolgus monkey in conjunction with GLP toxicology study. The PK and TK collected from these studies indicate that Hu5F9-G4 exhibits a varied half-life ($t^{1/2}$), ranging from 6.35 to 320 hours following single and multiple doses. The volume of distribution approximated monkey serum volume, as expected for a monoclonal antibody. Half-life appears to increase and clearance appears to decrease with increasing dose and with repeated dosing, suggesting saturation of target-mediated clearance via the endogenous CD47 cellular sink. There was a notable incidence of confirmed antidrug antibodies (ADA)

in monkeys, particularly for doses at or below 10 mg/kg, which appeared to correlate with lower concentrations of Hu5F9-G4. Nevertheless, exposure was maintained for doses at or above 10 mg/kg throughout the duration of the treatment in the repeated-dose studies.

Nonclinical studies were performed in NHPs (cynomolgus and rhesus monkeys) to support the use of Hu5F9-G4 for intravenous administration for the duration of 8 weeks in the clinical trial. The GLP toxicology study was conducted in cynomolgus monkeys, with the dosing phase being 8 weeks in duration followed by an 8 week recovery period. In the GLP 8-week toxicology study, Hu5F9-G4 was administered to male and female cynomolgus monkeys via a 1-hour intravenous infusion using a priming/maintenance dose schedule for a total of 8 weeks. Hu5F9-G4 was administered as a priming dose (5 mg/kg) on Day 1, followed by maintenance doses of 5, 10, 50, or 100 mg/kg administered twice weekly on Days 8, 11, 15, 18, 22, 25, 29, 32, 36, 39, 43, 46, 50, and 53.

The primary treatment-related finding noted in this study (as well as the previous pilot toxicology studies) was decreases in red cell mass, including red blood cell (RBC) count, hemoglobin, and hematocrit. The decreased hemoglobin was noted in all Hu5F9-G4-treated animals following the administration of the priming dose on Day 1, and the decrease in hemoglobin was generally most pronounced following administration of the first maintenance dose on Day 8. The severity and incidence of the Hu5F9-G4-related anemia varied across animals, and while the decreased hemoglobin did not occur in a clear dose dependent manner, the high-dose maintenance group (100 mg/kg) had the highest incidence of animals having a hemoglobin level 10.0 g/dL on Day 11 (90%). Importantly, the hemoglobin levels showed a trend toward recovery across all animals (generally starting around Days 15-32) and continued to recover to the end of the study. Due to severe anemia (hemoglobin≤7.0 g/dL), two animals (one in the 5/50 mg/kg group and one in the 5/100 mg/kg group) were placed on dose holiday to evaluate the recovery of the anemia and how the animals responded once dosing resumed. The decrease in hemoglobin level for the animal in the 50 mg/kg maintenance dose group was as low as 5.7 g/dL on Days 15 and 18, and thus, had dose holidays on Day 25-36 (maintenance doses 6-9). The hemoglobin for this animal began to recover on Day 36, and thus, dosing resumed for this animal on Day 39 (Dose 10). Even though the maintenance dosing resumed, the hemoglobin level for this animal continued to recover until the end of the study. The hemoglobin level for the animal in the 100 mg/kg maintenance dose group dropped to 6.9 g/dL on Day 18, and thus was placed on dose holiday on Day 25; this animal continued on dose holiday until the end of the study. The hemoglobin levels for this animal also showed a continued trend to recovery until the end of the study.

Thus, while it appears that a small number of animals may be especially sensitive to the anemia produced by Hu5F9-G4, no clinical signs of toxicity were observed in these animals, and furthermore, the anemia is transient and the hemoglobin levels recover over time. In addition to the decreases in red cell mass, increases in reticulocytes were observed in all Hu5F9-G4-treated groups, which is indicative of a robust erythropoietic response associated with the decreases in RBC mass.

Consistent with the previous studies, the decreased red cell mass was also associated with decreases in mean corpuscular volume (MCV) and haptoglobin and increases in mean corpuscular hemoglobin concentration (MCHC), reticulocytes, and red cell distribution width (RDW). Notably, free plasma hemoglobin was not observed in any Hu5F9-G4-treated groups, which is indicative of an absence of intravascular hemolysis. Minimal to mild increases in lymphocytes were also observed, but these increases were transient and sporadic in nature and did not occur in a dose-dependent manner. Changes in blood cell morphology were considered to be associated with accelerated red blood cell destruction/clearance and increased erythropoiesis, and included anisocytosis, spherocytes (microcytes), eccentrocytes, atypical erythrocyte fragments consistent with erythrocyte injury/clearance, erythrocyte clumping and large platelets, as well as changes associated with increased erythropoiesis consisting of anisocytosis and polychromatophilic macrocytes.

All of treatment-related changes in hematology parameters, including blood cell morphology, showed a continued trend toward recovery to the end of the study. Changes in bone marrow smear evaluations were limited to minimal to mild morphologic changes in the erythroid lineage (dysplasia), which consisted of occasional cells with abnormal nuclear shapes, multiple nuclei, nuclear blebbing, and/or nuclear to cytoplasm maturation asynchrony (abnormal nucleus to cytoplasm maturation). Marked reticulocytosis was associated with the treatment-related decreases in red cell mass, which is indicative of accelerated erythropoiesis. Additional changes considered to be related to the accelerated erythropoietic response associated with Hu5F9-G4 included mild decreases in the mean M:E ratio along with an appropriate minimal to mild shift to more immature erythroid precursors associated with accelerated erythropoiesis. Consistent with previous studies, treatment-related changes in hematology parameters (i.e., decrease hemoglobin; increased reticulocytes) observed in the GLP 8-week study were associated with increases in total bilirubin and decreases in haptoglobin.

Other changes in clinical chemistry parameters were observed only in the 100 mg/kg maintenance dose group, and included a slight decrease in albumin (two female animals), a slight increase in globulin, and a corresponding decrease in albumin:globulin ratio. All treatment-related changes in clinical chemistry parameters were partially or completely reversible at the end of the dosing phase.

Based on the known role of CD47 in the normal clearance of aging red blood cells, the Hu5F9-G4-related anemia observed in this study is considered related to the pharmacological action of Hu5F9-G4 binding to CD47 expressed on RBCs. We hypothesize that the administration of Hu5F9-G4 accelerates the process of elimination of aging RBCs by substituting gradual loss of CD47 with immediate blockade of CD47 on aging RBCs. The premature loss of aging RBCs is compensated by an ensuing reticulocytosis (which was observed across all studies), and over time, the initial anemia resolves as the aged RBCs are replaced with younger cells, and as a result, the age distribution of the RBC pool is shifted to younger cells.

Overall, administration of Hu5F9-G4 via a 1-hour IV infusion at a priming dose of 5 mg/kg in Week 1 (Day 1), followed by twice weekly maintenance doses for 7 consecutive weeks at doses up to 100 mg/kg, was clinically well tolerated in cynomolgus monkeys. Despite the treatment-related anemia, no signs of clinical toxicity were observed, including in the animals having dose holidays due to the severe anemia observed. The hematology changes observed in this study were consistent with previous studies and considered to be related to the pharmacological action of Hu5F9-G4 in accelerating the process of aging RBC elimination through binding of Hu5F9-G4 to CD47 expressed on RBCs. All treatment related changes in hematology and clinical chemistry parameters were partially or completely reversible by the end of the study. Therefore, based on the totality of the data, the highest non-severely-toxic-dose (HNSTD) for this study was considered to be the priming/maintenance dose of 5/100 mg/kg, the highest dose evaluated. The predicted safety margin (based on AUC) provided by the 100 mg/kg maintenance dose is more than adequate and ranges from 766- to 803-fold above the starting dose of 0.1 mg/kg for the proposed clinical study.

The humanized anti-CD47 antibody, Hu5F9-G4, was tested for its effects on pre-transfusion blood typing and cross-matching in preparation of strategies for management of patients who might need transfusion during Hu5F9-G4 treatment. Results showed that Hu5F9-G4 did not interfere with plasma antibody screening, making it possible to detect alloantibodies and to proceed with packed red blood cell (PRBC) transfusion if medically required. However, in whole blood Hu5F9-G4 interfered with the results for ABO blood typing, direct antiglobulin test (DAT), and red blood cell (RBC) immunophenotyping. Therefore, it will be important to have ABO blood typing, DAT, and RBC immunophenotyping performed on blood samples obtained prior to initiation of Hu5F9-G4 treatment. Hu5F9-G4 was incubated with RBCs from non-human primates and human donors. Hu5F9-G4 did not induce in vitro hemolysis of human RBCs, even in the presence of complement-containing serum. The study showed no evidence of hemagglutination (HA) in seven NHP specimens. However, HA was observed in all 14 human donor blood samples in the presence of 10 micrograms/mL of Hu5F9-G4.

Unlike most cases of agglutination-related autoimmune hemolytic anemia where HA is caused by cold IgM agglutinins, the agglutination caused by Hu5F9-G4, an IgG4, occurred at 37° C. but not at 4° C. While RBC agglutination can be seen in several conditions (usually in association with infectious agents, both with and without clinical sequelae), the clinical significance of the agglutination seen here is uncertain.

This is an open label, non-randomized, Phase 1, first-in-human, escalating dose cohort study of the CD47 blocking antibody Hu5F9-G4. The expected DLT of this drug is anemia, due to phagocytosis of senescent erythrocytes by macrophages. Pilot toxicology studies conducted in cynomolgus monkey studies showed that administration of a priming low dose of antibody produced a modest anemia and a reticulocyte response that enabled subsequent higher maintenance doses of drug to be well tolerated. Therefore, the strategy in this Phase 1 trial is to first establish an optimal priming dose in an escalating dose cohort design (Part A) at which 6 of 6 patients maintain a hemoglobin of 8 g/dL or greater in the absence of transfusion for the first four weeks and that produces a DLT, other than anemia, in no more than 1 of 6 patients. Once this optimal priming dose is established in Part A, it will be administered Day 1 of Week 1, to be followed one week later by weekly maintenance dosing in Part B, and if necessary, by Part C (twice weekly loading dosing for Weeks 2-4, followed by weekly maintenance dosing). The initial dose of 0.1 mg/kg in the first cohort is supported by a safety margin of 766-fold to 803-fold relative to the 100 mg/kg twice-weekly maintenance dose, which is the HNSTD in the pivotal GLP toxicology study. Based upon these studies, and assuming linear scaling of the safety margins (which may not be applicable), we expect that Hu5F9-G4 will be clinically tolerated at doses up to 10 mg/kg and perhaps higher. Therefore, a dose escalation schema of 0.1, 0.3, 1, 3, 10, and 20 mg/kg was selected.

For Part A, for the first patient in each cohort, evaluation for DLTs will be completed on Day 29 prior to enrollment of the second patient on the cohort. The second patient in a cohort of 3 will not be able to begin treatment until 2 weeks after the first patient has begun the DLT assessment period (14 days from start of therapy). The third patient can begin 4 weeks after the first patient has begun the DLT assessment period (28 days from the start of therapy). For Parts B and C, for the first patient in each cohort, evaluation for DLTs will be completed on Day 29 prior to enrollment of the second patient on the cohort. Subsequent patients on each cohort can begin treatment two weeks after the preceding patient starts therapy. In addition, the third patient in the cohort will require observation for 28 days prior to either proceeding to the next cohort or expansion to a cohort of 6. If a cohort is expanded from 3 to 6 patients, those patients can be treated 28 days after the third patient has initiated therapy, without an additional observation period between the fourth and sixth patients in that cohort. Dose level allocation will be decided by the CTMC.

This is a single center, open-label trial with three parts. The following apply to all parts of the study: Dose escalation will proceed through the designated dose levels, and decisions regarding dose escalation will be based upon the first 4 weeks of treatment in the current cohort, referred to as the "Dose Limiting Toxicity (DLT) Assessment Period," in conjunction with ongoing assessments for patients on prior cohorts who continued therapy beyond 4 weeks. Decisions regarding additional cohorts to further refine the MTD or RP2DS will be made by the CTMC and will require a study amendment.

Definition of Dose Limiting Toxicity (DLT). A DLT is defined as a possibly, probably, or definitely drug related adverse event (AE), occurring within the first four weeks of therapy, as follows: AE of Grade 3 or greater with exceptions listed below; Anemia as a consequence of the IMP is considered a Grade 3 toxicity if transfusion is indicated, irrespective of level of hemoglobin. Any transfusions or Grade 3 or greater severity of anemia or the need to utilize erythropoiesis stimulating agents will be considered a DLT and will lead to removal from the study protocol. The following will not be considered DLT and are excluded from the DLT definition: Grade 3 nausea in patients who have not received optimal treatments with antiemetics, and that resolves to <Grade 2 within 48 hours; Grade 3 vomiting in patients who have not received optimal treatment with anti-emetics, and that resolves to <Grade 2 within 48 hours; Grade 3 diarrhea in patients who have not received optimal treatment with anti-diarrheals, and that resolves to <Grade 2 within 48 hours; Grade 3 fatigue that resolves within two weeks on study; Grade 3 infusion reactions in the absence of pretreatment. Grade 3 increase in indirect/unconjugated blood bilirubin that resolves to baseline or Grade 1 within 7 days or prior to the next scheduled Hu5F9-G4 dose, whichever is sooner and the increase in indirect/unconjugated bilirubin is not temporally associated with a Grade 2 or higher increase in AST, ALT, and/or alkaline phosphatase from hepatic source (fractionation of alkaline phosphatase to determine origin is at the discretion of the investigator). Criteria for severity grading of indirect/unconjugated and direct/conjugated bilirubin will use CTCAE 4.03 criteria as it would apply to blood bilirubin. An increase in total bilirubin will not be a DLT if direct/conjugated bilirubin is Grade 2 or lower and indirect/unconjugated bilirubin elevation has been determined to not be a DLT.

Definition of Maximum Tolerated Dose (MTD). The optimal priming dose for Week 1, Day 1 in Parts B and C will be selected as the maximum dose in Part A at which 6 of 6 patients did not require blood product transfusion and maintained a hemoglobin greater than or equal to 8 g/dL (Grade 0-2 anemia) and with no more than 1 of 6 patients with a DLT other than anemia during the first 4 weeks of treatment. The MTD for Parts B and C is defined as the maximum dose level at which no more than 1 of 6 patients experienced a DLT and below the dose level at which 2 or more patients experienced a DLT for those patients who receive at least one maintenance dose of Hu5F9-G4. AEs that occur for patients in Part B and C who do not receive at least one maintenance dose (for Part B) or at least one loading dose (for Part C) will not be included in the MTD assessment for selection of the maintenance (Part B) or loading (Part C) doses. It is possible that an MTD will not be achieved in Parts B or C, in which case the maximum administered tolerated dose will be determined. The maximum planned weekly maintenance dose is 20 mg/kg.

Patient Evaluability. All patients exposed to the IMP, Hu5F9-G4, will be evaluable for safety and contribute data to dose escalation decisions. Patients who (1) decline participation and do not experience a DLT, or (2) are removed from the study for reasons not related to Hu5F9-G4 related AEs, or (3) have an AE not related to Hu5F9-G4 that requires removal from study before completion of the first four weeks of therapy, may be replaced by adding another patient to that cohort.

Drug Administration. Hu5F9-G4 will be administered intravenously. For Part A: The durations of the IV infusions of Hu5F9-G4 will be 60 minutes (±10 minutes) for the doses from 0.1 to 1 mg/kg and two hours (±10 minutes) for doses greater than 1 mg/kg.

For Parts B and C: The priming dose is the first dose that subjects in Parts B and C will receive and was determined to be 1 mg/kg at the completion of Part A. For subjects in Parts B and C, the duration of the infusion of the priming dose, namely 1 mg/kg, will be three hours. The maintenance doses will be administered after the completion of the priming dose. The duration of the infusion of the maintenance doses will be two hours for doses greater than 1 mg/kg. Patients with dose delay or drug holiday of 2 weeks or longer will be re-primed in which case the priming dose of 1 mg/kg will be administered over three hours prior to resumption of the assigned maintenance dose. Premedication may be administered prior to the second or subsequent doses for patients who experience an infusion reaction to previous Hu5F9-G4 administration. The suggested premedication regimen could include a combination of acetaminophen 500 mg PO, dexamethasone 8 mg IV, and diphenhydramine 25 mg IV administered 30 minutes prior to the infusion of Hu5F9-G4. In the case of an infusion reaction, a premedication regimen for subsequent treatments is at the discretion of the investigator.

Identification of Priming Dose

The overall aim of this portion of the study is to identify the priming dose that results in an acceptable level of anemia (less than Grade 3) within the first 4 weeks in all 6 patients of the dose-defining cohort. Thus, the optimal priming dose level will be the maximum dose level at which all 6 patients maintain a hemoglobin of 8 g/dL or greater in the absence of transfusion for the first four weeks and which produces a DLT other than anemia in no more than 1 of 6 patients. Patients will be assessed in successive dose cohorts as follows: 0.1, 0.3, 1, 3, 10, and 20 mg/kg administered as an IV infusion. Dose escalation in Part A will follow a modified accelerated titration design for dose levels below 3 mg/kg and the standard 3 plus 3 dose escalation design for dose levels at 3 mg/kg and above. For the accelerated titration design, one patient will be enrolled per cohort until a Grade 2 or greater AE related to Hu5F9-G4 is observed within the first four weeks. Such an event will result in cohort expansion to 3 patients. However, any occurrence of Grade 3 anemia in the first four weeks for any patient in Part A will result in cessation of further accrual into that cohort and will result in expansion of the next lower dose cohort. For AEs other than anemia, one patient with DLT (Grade 3 or greater AE related to Hu5F9-G4) in the first three patients will result in a cohort expansion to 6 patients. Two patients with DLT indicate that the maximum tolerated priming dose has been exceeded, further enrollment to that cohort will not be permitted, and the next lower dose cohort, if it contains 3 or fewer patients, will be expanded to 6 patients. Patients enrolled in Part A will continue weekly treatment at the assigned dose level until unacceptable toxicity or documentation of progressive disease (as determined by RECIST v 1.1 for solid tumors or the IWG criteria for lymphomas) or voluntary patient withdrawal from the study. Except for the priming dose on Day 1 of Part B and C, followed by higher maintenance and/or loading doses, there will be no intrapatient dose escalation in this study. Please note that any Grade 3 anemia in the first 4 weeks of Part A will trigger cessation of the cohort and expansion of the next lower dose cohort. Moreover, the accelerated titration design only applies to dose levels below 3 mg/kg. Dose levels of 3 mg/kg or greater will be performed with a standard 3 plus 3 design. After completion of Part A and per protocol Amendment 4.0, the priming dose was identified as 1 mg/kg. In addition, ongoing weekly treatment with 1 mg/kg in Part A established that 1 mg/kg is also safe as a maintenance dose.

Expanded Safety Assessment of the Priming Dose During Parts B and C. Patients in Parts B and C will receive the optimal priming dose of 1 mg/kg on Week 1, Day 1 that was determined from Part A, followed by weekly maintenance doses starting on Day 8. If an AE or SAE occurs after a patient receives the priming dose but before the patient receives a maintenance dose then this AE or SAE will be attributed to the priming dose and contribute to the expanded safety assessment of the priming dose. SAEs and AEs attributed to the priming dose will continue to be closely monitored by the CTMC with meetings to convene on a regular basis or more frequently if necessary (as per the CTMC charter).

Part B: Identification of the MTD for Weekly Maintenance Dosing After a Single Priming Dose. All patients in Part B will receive the optimal priming dose on Week 1, Day 1 that was determined from Part A, followed by weekly maintenance doses starting on Day 8. The weekly maintenance dose administered is determined by the assigned Part B dose cohort. The original proposed dose cohorts for Part B were 0.3, 1, 3, 10, and 20 mg/kg. Weekly maintenance dose cohorts will begin at the dose that is one dose level higher than the optimal priming dose. The Part A 1 mg/kg dose level was determined to be the optimal priming dose and weekly maintenance dosing at 1 mg/kg was determined to be safe; therefore, the first maintenance dose level assigned in Part B will be the 3 mg/kg IV weekly dose level and maintenance dose levels 0.3 and 1 mg/kg will be skipped. Dose escalation in Part B will follow a standard 3 plus 3 dose escalation design. The MTD for Part B is the maximum dose level at which no more than 1 of 6 patients experiences a DLT and below the dose level at which 2 or more patients experience a DLT for those patients who receive at least one maintenance dose of Hu5F9-G4. AEs that occur for patients in Part B who do not receive at least one maintenance dose of Hu5F9-G4 will not be included in the DLT assessment for selection of the maintenance dose. To further refine the MTD, a dose level midway between the nominal MTD and the next higher dose level may be tested. For example, if two or more subjects at the 3 mg/kg dose level experience a DLT attributed to the maintenance dose, a dose level midway between 1 mg/kg and 3 mg/kg, namely 2 mg/kg, may be tested to further refine the MTD allowing the final MTD determination to be increased from 1 mg/kg to 2 mg/kg if no more than 1 of 6 subjects at 2 mg/kg experience a DLT at 2 mg/kg. Similarly, dose levels of 6.5 mg/kg and 15 mg/kg may be added if the nominal MTD is 3 mg/kg or 10 mg/kg, respectively. It is possible that an MTD will not be achieved in Part B for the maintenance dose, in which case the maximum administered tolerated dose will be determined because the maximum weekly dose will be 20 mg/kg. The DLT assessment period for the maintenance dose on Part B will start from the time of administration of the first maintenance dose (Week 2, Day 8) until one week after the completion of the third maintenance dose (Week 4, Day 29). Patients enrolled in Part B will continue weekly treatment at the assigned dose level until unacceptable toxicity or documentation of progressive disease as determined by RECIST v 1.1 for solid tumors, or IWG criteria for lymphomas, or voluntary patient withdrawal from the study. Except for the priming dose on Day 1 of Part B and C, followed by higher maintenance and/or loading doses, there will be no intra-patient dose escalation in this study. The PK targets for the RP2DS are the achievement and maintenance of a trough level of the Hu5F9-G4 antibody above 100 micrograms/mL in plasma in five of six patients at the RP2DS. When the MTD or maximum administered tolerated dose (in the absence of an MTD) or optimal biological (based on PK) dose for weekly administration has been determined, the study may be amended to add additional cohorts to Part B where weekly dosing is followed by Q14 and/or Q21 day dosing. The more prolonged schedules would be initiated only after detailed review of available safety, PK, and pharmacodynamics data. For example, this could be initiated when PK parameters indicate saturation of target-mediated clearance and prolongation of Hu5F9-G4 half-life. Dosing during the Q14 or Q21 day interval cohorts may be increased to 30 mg/kg, by protocol amendment if 20 mg/kg is well tolerated.

Part C: Identification of the MTD for Twice Weekly Loading Dosing, After an Initial Priming Dose and Prior to Weekly Maintenance Dosing, if Adequate PK Parameters are not Achieved in Part B by Weekly Dosing. Part C may be initiated if adequate exposure to Hu5F9-G4 is not achieved in Part B. Adequate exposure is defined as a trough level of antibody above 100 micrograms/mL achieved in five of six patients at the recommended Phase 2 dose by Day 57. All patients in Part C will receive the optimal priming dose determined in Part A on Week 1, Day 1, followed by twice weekly loading doses according to the assigned Part C dose cohort. SAEs and AEs attributed to the priming dose will continue to be closely monitored by the CTMC with meetings to convene on a regular basis or more frequently if necessary as needed (as per the CTMC charter). The original proposed dose cohorts for Part C were 0.3, 1, 3, 10, and 20 mg/kg. Twice weekly loading dose cohorts will begin at the dose level that is one level lower than the Part B MTD or the maximum administered tolerated dose. Thus, if 20 mg/kg was the MTD in Part B, the twice weekly loading dose in Part C will be 10 mg/kg. Twice weekly loading doses (administered the first and fourth day of each weekly period) will be administered during Weeks 2, 3, and 4. This will be followed by weekly maintenance doses in Weeks 5-8. After the completion and analysis of Hu5F9-G4 serum concentrations within the proposed cohorts in Part C and in the event that adequate exposure is not achieved during twice weekly administration at the end of three weeks of loading (Weeks 2-4), the protocol may be amended to include cohorts of twice weekly loading dosing for additional 2-week periods beyond Week 4. Dose levels higher than 20 mg/kg for either loading or maintenance in Part C will require a protocol amendment. Similarly to Part B, additional cohorts may be added to Part C when the MTD or maximum administered tolerated dose (in the absence of MTD) or optimal biological dose has been determined, where twice weekly loading dosing, then weekly maintenance dosing, is followed by Q14 or Q21 day dosing based on safety, PK, and pharmacodynamics data. For example, a more prolonged schedule would begin at a time point when PK parameters indicate saturation of target-mediated clearance and prolongation of Hu5F9-G4 half-life. The dose employed for the Q14 day or Q21 day cohorts may be increased to 30 mg/kg, by protocol amendment, if 20 mg/kg is well tolerated. Dose escalation in Part C will follow a standard 3 plus 3 design for all dose levels. DLT assessment towards the MTD will apply for those patients who receive at least one loading dose for Part C. DLTs that occur for patients in Part C who do not receive at least one loading dose of Hu5F9-G4 will not be included in the DLT assessment for identification of the MTD for the loading dose. If no patients experience a DLT, then dose escalation may proceed to the next higher dose level. If one of three patients experiences a DLT, then that same dose level cohort will be expanded to 6 patients. If 2 or more of 6 patients experiences a DLT, then no further enrollment will be permitted at that dose level and the MTD will have been exceeded. The MTD for Part C is the maximum dose level at which no more than 1 of 6 patients experiences a DLT and below the dose level at which 2 or more of 6 patients experiences a DLT. The DLT assessment period for the loading dose on Part C will start from the time of administration of the first loading dose (Week 2, Day 8) until Week 4, Day 29. Patients enrolled in Part C will continue treatment at the assigned dose level until unacceptable toxicity or documentation of progressive disease as determined by RECIST v 1.1 for solid tumors or by IWG criteria for lymphomas or voluntary patient withdrawal from the study.

Intra-Patient Dose Escalation. Except for the priming dose on Day 1 of Part B and C, followed by higher maintenance and/or loading doses, there will be no intra-patient dose escalation in this study.

Investigational Agent

The active pharmaceutical ingredient (API) is Hu5F9-G4, a humanized monoclonal antibody of the IgG4 kappa isotype containing a Ser-Pro (S-P) substitution in the hinge region of the heavy chain to reduce Fab arm exchange. It is comprised of a disulfide-linked glycosylated tetramer consisting of two identical 444 amino acid heavy gamma chains and two identical 219 amino acid kappa light chains. Hu5F9-G4 targets CD47. Hu5F9-G4 drug product is provided in a liquid dosage form intended for IV infusion. Hu5F9-G4 is supplied in single-use, 10 mL vials containing 200 mg of the antibody, in a formulation of 10 mM sodium Acetate, 5% (w/v) sorbitol, 0.01% (w/v) polysorbate 20, pH 5.0.

Hu5F9-G4 drug substance has been manufactured at Lonza Group, Ltd (Slough, UK), and drug product has been manufactured by Patheon UK Limited (Swindon, UK). The drug product, referred to as IMP throughout this document, will be supplied by the Sponsor of this trial, Stanford University, via a storage and distribution contract with Fisher BioServices.

Details of Administration of Hu5F9-G5

Dose Calculation. The individual dose is calculated using the actual body weight of the patient at enrollment (using weight obtained at either Screen or Day 1), and the dose may remain constant throughout the study unless a greater than 10% change in weight is observed. The following formula should be used to calculate the volume of Hu5F9-G4 from the vials containing 20 mg/mL (200 mg total of Hu5F9-G4 per vial) required for each administration: Body Weight (kg)×Desired Dose (mg/kg)=Volume of Hu5F9-G4 (mL) 20 mg/mL For Part A: For dose-escalation patients requiring a dose of 1 mg/kg or less, Hu5F9-G4 will be administered as a continuous IV infusion in 250 mL over 60 minutes (±10 minutes). All other infusions for doses greater than 1 mg/kg will be administered in 500 mL over 2 hours (±10 minutes).

For Parts B and C: The priming dose is the first dose that patients in Parts B and C will receive and was determined to be 1 mg/kg at the completion of Part A. SAEs and AEs attributed to the priming dose will continue to be closely monitored by the CTMC with meetings to convene on a regular basis or more frequently as needed (as per the CTMC charter). For subjects in Parts B and C, the duration of the infusion of the priming dose, namely 1 mg/kg, will be three hours. In Part B, the maintenance doses will be administered starting on Day 8, one week after the completion of the priming dose. The duration of the infusion of the maintenance doses will be two hours for doses greater than 1 mg/kg. In Part C, the loading doses will be administered starting on Day 8, one week after the completion of the priming dose, and the maintenance doses will be administered starting on Day 29. The duration of the infusion of the loading and maintenance doses will be two hours for doses greater than 1 mg/kg.

Patients in Parts B and C with dose delay or drug holiday of 2 weeks or longer will be reprimed in which case the priming dose of 1 mg/kg will be administered over three hours prior to resumption of the assigned maintenance dose; for patients in Part A the re-priming infusion duration will be one hour as per protocol. Hu5F9-G4 should NOT be administered as a bolus injection.

Adjustments to the dosing schedule will be allowed for treatment-related toxicity as follows: No treatment delays are acceptable for the first four weeks of treatment. Thereafter, treatment may be delayed for up to three weeks to allow sufficient time for recovery from non-DLT treatment-related toxicities. Patients who develop Grade 2 anemia may have a treatment delay of up to three weeks beginning at Week 5 to allow for recovery of the anemia to Grade 1. However, any DLT will require removal of the patient from the study. Treatment delays for more than three weeks (such as for an unrelated medical condition with expected recovery) must be approved by the CTMC. Additionally, drug holidays for up to 2 weeks will be allowed after Day 57 at the discretion of the investigator and with written Sponsor approval. "Drug Holiday" is defined as a holiday from protocol specified treatment, assessments, and procedures. There must be a minimum of 6 days between Hu5F9-G4 infusions in Parts A and B and a minimum of 3 days between Hu5F9-G4 infusions delivered by twice weekly infusions. Patients in Parts B and C with a treatment delay or holiday of 2 weeks or more must be "reprimed" by receiving the priming dose of 1 mg/kg IV over three hours again prior to resuming the assigned maintenance treatment dose; for patients in Part A the re-priming infusion duration will be one hour as per protocol.

Receptor Occupancy Assay

Receptor occupancy samples will be drawn per the schedule of assessments. Blood cells will be analyzed by flow cytometry for CD47 receptor occupancy in the white blood cell and red blood cell fractions. The baseline (Day 1) sample from each patient, collected prior to the first Hu5F9-G4 antibody incubation, will be incubated with increasing concentrations of Hu5F9-G4 antibody to establish a standard curve for CD47 molecule/receptor occupancy. In addition, phosphatidylserine expression on red blood cells may be assessed by annexin V expression at baseline (Day 1) and on Day 8, which can be completed as an additional aspect of the receptor occupancy assay without additional blood draws.

CD47 receptor occupancy will be determined on primary cancer cells by flow cytometry or immunofluorescence on samples obtained from malignant effusions or tissue biopsies, when available.

Changes in the immune cell compartment composition in the tumors will be determined in tumor biopsies collected before and after treatment, when available.

Association of somatic cancer mutations with response to Hu5F9-G4. For example, colorectal, lung, and head and neck tumors may be analyzed for KRAS, BRAF, NRAS, and/or PIK3CA mutations.

Response to Hu5F9-G4 treatment for individual study patients utilizing in vitro assays and xenotransplantation mouse studies.

Assessment of potential resistance to Hu5F9-G4 and exploration of alternative CD47 blocking strategies to overcome resistance (e.g., high affinity SIRP-alpha Fc fusion proteins).

Peripheral Blood Smear Assessment: Peripheral Smears will be assessed for the presence of hemagglutination in addition to standard cell morphology assessment. These labs should be drawn in the arm contralateral to the drug infusion if possible. For the first 2 weeks of treatment in Parts A and B, peripheral smears will be performed on Days 1 and 8 pre-dose and 4 hours after the end of each IMP infusion (±30 minutes), Days 2 and 9 at 24-hour post IMP infusion (±4 hours), Days 4 and 11 at the 72-hour time point (±24 hours). In Part A after Week 2, peripheral smears will be performed pre-dose on Day 15 and thereafter at the discretion of the investigator. In Part B after Week 2, peripheral smears will also be performed pre-dose on Days 15 and 22, but for D15 peripheral smear will also be performed 4 hours after the end of the infusion (±30 minutes). For Days 29 and following, peripheral smears will be performed at the discretion of the investigator and at the End of Study Visit. In Part C, peripheral smears will be performed on Days 1 and 8 pre-dose and 4 hours after the end of the IMP infusion (±30 minutes), Days 2 and 9 at 24-hour post IMP infusion (±4 hours), Day 4 at the 72-hour time point (±24 hours), and will also be performed pre-dose and at 4 hours after the end of the IMP infusion (±30 minutes) on Days 11, 15, 18, 22, 25 and 29. For Days 30 and following, peripheral smears will be performed at the discretion of the investigator and at the End of Study Visit. For patients undergoing blood transfusion, peripheral smears will be performed prior to blood transfusion and again 4 hours (±30 minutes) after completion of the transfusion.

Pharmacokinetic Analyses

The Safety Analysis Set will be included in the populations for PK, CD47 receptor occupancy, immunogenicity, and exploratory biomarkers if data are available for analysis.

In addition, the PK population requires sufficient measureable concentration data for the estimation of PK parameters, while the PK concentration population will include all patients with any measurable concentrations of Hu5F9-G4. The inclusion of patients with protocol violations will be assessed on a patient-by-patient basis for inclusion in the PK population prior to the analysis. Concentration versus time data will be summarized descriptively, including N, Mean, SD, Geometric Mean, Median, Min, Max and % CV. Individual and mean Hu5F9-G4 concentration versus time curves will be graphically presented. Pharmacokinetic parameters to be calculated using non-compartmental methods include the following: $C_{max}$, $T_{max}$, $t^{1/2}$, area under the serum concentration time curve from time zero to the last measurable concentration ($AUC_{0-t}$), AUC from time zero to infinity ($AUC_{0-\infty}$), clearance (CL), and volume of distribution ($V_{ss}$, $V_z$). All PK parameters, including exposure ($C_{max}$, AUCs) to Hu-5F9-G4 will be summarized for individual patients and by dose cohorts. Exploratory analyses may be conducted to assess the relationship between one or more PK parameters and selected safety and efficacy measures (for example, hemoglobin, reticulocytosis, receptor saturation by flow cytometry, or immunogenicity).

Immunogenicity Assessments

The rate and magnitude of anti-Hu5F9-G4 antibody positivity will be evaluated for individual patients, for each Part A, B, C/dose level, and for the pooled patient population. Exploratory evaluations may be conducted to determine the relationship between immunogenicity assay positivity and one or more safety, PK, or efficacy parameters (for example, drug clearance, AEs, tumor response).

Anti-Tumor Activity

Analysis of tumor response will be conducted for the Evaluable for Tumor Assessment Set. The RECIST v 1.1 or the IWG criteria will be applied, and assessment will be per the investigator. The proportion of patients with CR, PR, SD, stable disease sustained for 6 months (SD6), and PD will be calculated at each time point. Objective response will be calculated as the CR+PR with the 95% confidence intervals for each Part A, B, C/dose level and overall for each measurement time point will be tabulated. The proportion of patients defined as achieving clinical benefit will be calculated as the CR+PR+SD6 with the 95% confidence intervals. Best Overall Response will also be evaluated. Duration of response will be calculated from the time that initial response was first identified until the development of PD. Progression is assessed relative to the smallest tumor measurement. Details with regard to the analysis of antitumor activity will be specified in the SAP.

In summary, based on the results from the toxicology studies, the nonclinical safety assessment program supports the administration of Hu5F9-G4 (e.g., as an IV infusion) for a clinical trial.

Example 4

In preclinical trials, a serum level of greater than 100 µg/mg has been shown to be therapeutically effective. The data provided in FIG. 9 demonstrates a dose in human patients that provides for this level of drug.

Figure 9:
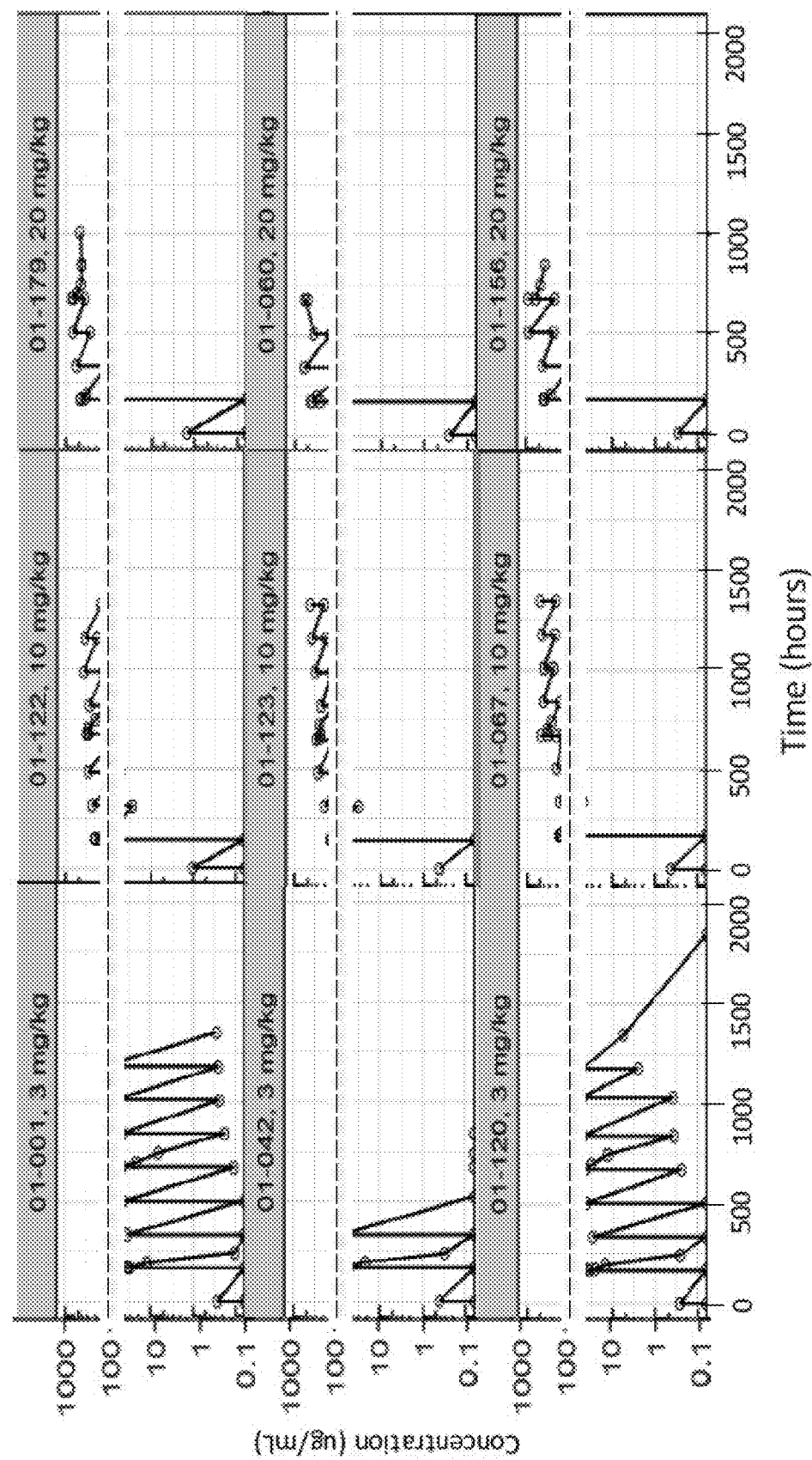
FIG. 9. Hu5F9-G4 can achieve target PK levels at clinically feasible doses. The data show Hu5F9-G4 can saturate the internal CD47 tissue sink at clinically feasible doses; and antibody half-life is extended after saturation of the tissue sink has occurred.

Shown in FIG. 9, each of the graphs represents a dosing cohort of human patients with solid tumors, treated with 1 mg/kg priming dose of 5F9 and the indicated maintenance doses. Each line shows the mean value of the concentration of free drug (Hu5F9-G4) in µg/ml in a serum sample, with error bars for 3 patients. The values in the table below show the mean Cmax for each cohort at week 2 and the AUC last shows how long these have been maintained (hours).

The X axis of the graphs depicts the time of samples with respect to dosing, where 0 indicates the sample prior to infusion and the remaining are time points by hours post-infusion.

The line marked Week 2 depicts the concentration curve after the first maintenance dose at 3, 10, or 20 mg/ml (week one is the priming dose). The data for Week 5 represents the values after the fourth maintenance dose. The highest point of each curve determines the Cmax, and the slope curve determines the clearance or sustainment of the drug in the serum.

The data from a first maintenance dose of 3 mg/kg shows a rapid clearance from serum. This dose was also cleared fairly quickly even after week 5 of treatment. It may also be noted that a dose of 3 mg/kg does not achieve the targeted serum level of greater than 100 µg/ml, even as Cmax.

At a dose of 10 mg/kg a Cmax at/above 100 µg/ml was achieved, but the level was not sustained but it is not well sustained above 100 µg/ml with the clearance seen after the week 2 dose. The 10 mg/kg dose does provide for a more sustained level at week 5, which may be attributed to saturation of the CD47 sink with the repeated dosing schedule.

At a maintenance dose of 20 mg/kg, sustained serum levels above the targeted level of 100 µg/ml could be achieved with the first maintenance dose (week 2). As shown in FIG. 9, the curve is flat—almost horizontal.

What is claimed is:

1. A method of treating a human subject for multiple myeloma with a therapeutic dose of anti-CD47 antibody hu5F9-G4, the method comprising:
   (a) administering a priming dose of the hu5F9-G4 to the subject, where the priming dose is from about 0.5 to about 5 mg/kg, wherein the priming dose is administered to the human subject in an infusate with a concentration of from 0.05 mg/ml to 0.5 mg/ml hu5F9-G4 delivered over a period of at least 3 hours to reduce severity of hemagglutination; and
   (b) administering a therapeutically effective dose of hu5F9-G4 to the subject wherein the therapeutically effective dose is 10-40 mg/kg,
   wherein step (b) is after at least about 3 days after beginning step (a), wherein the priming dose primes the subject for administration of the therapeutically effective dose of anti-CD47 antibody such that the therapeutically effective dose does not result in a severe loss of red blood cells.

2. The method of claim 1, further comprising after step (a) and prior to step (b): a step of determining whether administration of the priming dose was effective.

3. The method of claim 2, wherein the determining step comprises performing a reticulocyte count, wherein administration of the primer agent is determined to have been effective if the reticulocyte count is from about $100 \times 10^9$ reticulocytes per L to about—$1000 \times 10^9$ reticulocytes per L.

4. The method of claim 2, wherein the determining step comprises performing a reticulocyte count, wherein administration of the primer agent is determined to have been effective if the percentage of reticulocytes in the blood is greater than about 1.5%.

5. The method of claim 2, wherein the determining step comprises performing a reticulocyte count, wherein administration of the primer agent is determined to have been effective if the reticulocyte index is greater than about 2%.

6. The method of claim 1, where the priming dose is delivered by continuous pump over a period of from 6 hours to 3 days.

7. The method of claim 1, wherein the priming dose is delivered subcutaneously.

8. The method of claim 1, wherein the priming dose is determined to saturate at least about 50% of CD47 sites of red blood cells.

9. The method of claim 8, wherein the dose is determined by a receptor occupancy assay, in which following administration of a dose of unlabeled anti-CD47 agent to the subject, a blood sample is obtained and combined with a saturating dose of detectably labeled anti-CD47 antibody; and determining the level of binding.

10. The method of claim 1, wherein the therapeutically effective dose of (b) is sufficient to achieve a circulating level of greater than 100 μg/ml of hu5F9-G4 agent for a sustained period of time.

11. The method of claim 10, wherein the sustained period of time is from about 1 week to about 2 weeks.

12. The method of claim 10, wherein the therapeutically effective dose is from about 10 mg/kg to about 25 mg/ml.

13. The method of claim 10, wherein the therapeutically effective dose is from about 17.5 mg/kg to about 20 mg/kg.

14. The method of claim 10, wherein the therapeutically effective dose is administered from about every 7 days to about every 14 days.

* * * * *